United States Patent
Kotmel et al.

(10) Patent No.: US 10,413,244 B2
(45) Date of Patent: Sep. 17, 2019

(54) METHOD AND APPARATUS FOR ENDOBRONCHIAL DIAGNOSIS

(71) Applicant: PulmonX Corporation, Redwood City, CA (US)

(72) Inventors: Robert Kotmel, Burlingame, CA (US); Peter Soltesz, Henderson, NV (US); Anthony Wondka, Thousand Oaks, CA (US); Rodney Perkins, Woodside, CA (US)

(73) Assignee: Pulmonx Corporation, Redwood City, CA (US)

( * ) Notice: Subject to any disclaimer, the term of this patent is extended or adjusted under 35 U.S.C. 154(b) by 0 days.

(21) Appl. No.: 14/919,480

(22) Filed: Oct. 21, 2015

(65) Prior Publication Data
US 2016/0038058 A1 Feb. 11, 2016

Related U.S. Application Data

(63) Continuation of application No. 10/241,733, filed on Sep. 10, 2002, now abandoned.
(Continued)

(51) Int. Cl.
*A61B 5/00* (2006.01)
*A61B 5/08* (2006.01)
(Continued)

(52) U.S. Cl.
CPC ............ *A61B 5/6853* (2013.01); *A61B 5/055* (2013.01); *A61B 5/08* (2013.01); *A61B 5/082* (2013.01);
(Continued)

(58) Field of Classification Search
CPC ... A61B 5/085; A61B 5/087; A61B 17/12104; A61B 5/08; A61B 17/12022;
(Continued)

(56) References Cited

U.S. PATENT DOCUMENTS

| | | |
|---|---|---|
| 3,322,126 A | 5/1967 | Rusch et al. |
| 3,498,286 A | 3/1970 | Polanyi et al. |

(Continued)

FOREIGN PATENT DOCUMENTS

| | | |
|---|---|---|
| EP | 0692273 A1 | 1/1996 |
| EP | 1078601 B1 | 10/2006 |

(Continued)

OTHER PUBLICATIONS

Airflow resistance in lower airway of the dog Robert G. Rossing Journal of Applied Physiology Published Nov. 1, 1962 vol. 17 No. 6, 877-884.*

(Continued)

*Primary Examiner* — Christian Jang
*Assistant Examiner* — Karen E Toth
(74) *Attorney, Agent, or Firm* — Wilson Sonsini Goodrich & Rosati

(57) ABSTRACT

The present invention provides systems, methods, devices and kits for assessing the level of pulmonary disease in individual lung compartments. A lung compartment comprises a subportion of a lung, such as a lobe, a segment or a subsegment, for example. By measuring individual lung compartments, the level of disease of the pulmonary system may be more precisely defined by determining values of disease parameters reflective of individual subportions or compartments of a lung. Likewise, compartments may be separately imaged to provide further measurement information. Once individual compartments are characterized, they may be compared and ranked based on a number of variables reflecting, for example, level of disease or need for treatment. Such comparison may be aided by simultaneous display of such variables or images on a visual display. Further, the same tests may be performed on the lung as a whole or on both lungs and to determine the affect of the (Continued)

diseased lung compartments on the overall lung performance. In addition, the diseased lung compartments may be temporarily isolated and the measurement tests performed to determine the affect of the isolation on overall lung performance. As a result, the most beneficial treatment options may be selected.

14 Claims, 21 Drawing Sheets

Related U.S. Application Data

(60) Provisional application No. 60/318,539, filed on Sep. 10, 2001.

(51) Int. Cl.

| | | |
|---|---|---|
| *A61B 6/00* | (2006.01) | |
| *A61B 8/12* | (2006.01) | |
| *A61B 5/055* | (2006.01) | |
| *A61B 5/083* | (2006.01) | |
| *A61B 5/085* | (2006.01) | |
| *A61B 5/087* | (2006.01) | |
| *A61M 16/04* | (2006.01) | |
| *A61M 25/00* | (2006.01) | |
| *A61M 25/10* | (2013.01) | |

(52) U.S. Cl.
CPC .............. *A61B 5/083* (2013.01); *A61B 5/085* (2013.01); *A61B 5/087* (2013.01); *A61B 5/0813* (2013.01); *A61B 5/7278* (2013.01); *A61B 5/742* (2013.01); *A61B 6/481* (2013.01); *A61B 6/485* (2013.01); *A61B 8/12* (2013.01); *A61M 16/04* (2013.01); *A61M 16/0404* (2014.02); *A61M 16/0459* (2014.02); *A61M 16/0486* (2014.02); *A61M 25/0026* (2013.01); *A61M 25/10* (2013.01); *A61B 2562/0247* (2013.01); *A61M 16/0434* (2013.01); *A61M 2016/0413* (2013.01); *A61M 2025/1052* (2013.01)

(58) Field of Classification Search
CPC .... A61B 17/12136; A61B 2017/22067; A61B 5/6853
See application file for complete search history.

(56) References Cited

U.S. PATENT DOCUMENTS

| | | | |
|---|---|---|---|
| 3,669,098 A | 6/1972 | Takahashi | |
| 3,677,262 A | 7/1972 | Zukowski | |
| 3,776,222 A | 12/1973 | Smiddy | |
| 3,866,599 A | 2/1975 | Johnson | |
| 3,913,568 A | 10/1975 | Carpenter | |
| 4,031,885 A | 6/1977 | Davis et al. | |
| 4,036,222 A * | 7/1977 | Gillard | A61B 5/085 |
| | | | 600/533 |
| 4,041,936 A | 8/1977 | Carden | |
| 4,121,583 A | 10/1978 | Chen | |
| 4,327,720 A | 5/1982 | Bronson et al. | |
| 4,327,721 A | 5/1982 | Goldin et al. | |
| 4,413,632 A | 11/1983 | Schlessinger et al. | |
| 4,453,545 A | 6/1984 | Inoue | |
| 4,468,216 A | 8/1984 | Muto | |
| 4,567,882 A | 2/1986 | Heller | |
| 4,716,896 A | 1/1988 | Ackerman | |
| 4,742,819 A | 5/1988 | George | |
| 4,784,133 A | 11/1988 | Mackin | |
| 4,796,639 A | 1/1989 | Snow et al. | |
| 4,819,664 A | 4/1989 | Nazari | |
| 4,846,153 A | 7/1989 | Berci | |
| 4,850,371 A * | 7/1989 | Broadhurst | A61B 5/0205 |
| | | | 128/207.14 |
| 4,862,874 A | 10/1989 | Kellner | |
| 4,896,941 A | 1/1990 | Hayashi et al. | |
| 4,949,716 A | 8/1990 | Chenoweth | |
| 4,955,375 A | 10/1990 | Martinez | |
| 4,958,932 A | 10/1990 | Kegelman et al. | |
| 4,961,738 A | 10/1990 | Mackin | |
| 4,972,842 A | 11/1990 | Korten et al. | |
| 4,976,710 A | 12/1990 | Mackin | |
| 5,056,529 A | 10/1991 | de Groot | |
| 5,146,916 A | 9/1992 | Catalani | |
| 5,143,062 A | 10/1992 | Peckham | |
| 5,187,579 A * | 2/1993 | Hiyama | A61B 1/00009 |
| | | | 348/588 |
| 5,285,778 A | 2/1994 | Mackin | |
| 5,309,903 A | 5/1994 | Long | |
| 5,331,947 A | 7/1994 | Shtunnan | |
| 5,361,753 A | 11/1994 | Pothmann et al. | |
| 5,447,165 A | 9/1995 | Gustafsson | |
| 5,477,851 A | 12/1995 | Callaghan et al. | |
| 5,499,625 A | 3/1996 | Frass et al. | |
| 5,540,229 A | 7/1996 | Collet-Billon et al. | |
| 5,598,840 A | 2/1997 | lund et al. | |
| 5,642,730 A | 7/1997 | Baran | |
| 5,645,519 A | 7/1997 | Lee et al. | |
| 5,653,231 A | 8/1997 | Bell | |
| 5,660,175 A | 8/1997 | Dayal | |
| 5,682,880 A | 11/1997 | Brain | |
| 5,692,497 A | 12/1997 | Schnitzer et al. | |
| 5,707,352 A | 1/1998 | Sekins et al. | |
| 5,738,090 A | 4/1998 | Lachmann et al. | |
| 5,752,921 A | 5/1998 | Orr | |
| 5,810,741 A | 9/1998 | Essen-Moller | |
| 5,972,026 A | 10/1999 | Laufer et al. | |
| 6,068,602 A | 5/2000 | Tham et al. | |
| 6,083,162 A | 7/2000 | Vining | |
| 6,083,255 A | 7/2000 | Laufer et al. | |
| 6,117,073 A * | 9/2000 | Jones | G06F 19/327 |
| | | | 600/300 |
| 6,155,252 A | 12/2000 | Warters | |
| 6,174,323 B1 | 1/2001 | Biggs et al. | |
| 6,287,290 B1 | 9/2001 | Perkins et al. | |
| 6,370,415 B1 | 4/2002 | Weiler et al. | |
| 6,629,951 B2 | 10/2003 | Laufer et al. | |
| 6,692,494 B1 | 2/2004 | Cooper et al. | |
| 6,709,401 B2 | 3/2004 | Perkins et al. | |
| 6,712,812 B2 | 3/2004 | Roschak et al. | |
| 6,749,606 B2 | 6/2004 | Keast et al. | |
| 6,878,141 B1 | 4/2005 | Perkins et al. | |
| 6,886,558 B2 | 5/2005 | Tanaka | |
| 6,904,909 B2 * | 6/2005 | Andreas | A61B 17/12104 |
| | | | 128/200.24 |
| 6,997,189 B2 | 2/2006 | Biggs et al. | |
| 7,022,088 B2 | 4/2006 | Keast et al. | |
| 7,086,398 B2 | 8/2006 | Tanaka | |
| 2002/0049370 A1 * | 4/2002 | Laufer | A61B 8/12 |
| | | | 600/300 |
| 2002/0198449 A1 | 12/2002 | Baumgardner et al. | |
| 2003/0016850 A1 | 1/2003 | Kaufman et al. | |
| 2003/0051733 A1 | 3/2003 | Kotmel et al. | |
| 2004/0073130 A1 | 4/2004 | Bohm et al. | |
| 2008/0200797 A1 | 8/2008 | Kotmel et al. | |

FOREIGN PATENT DOCUMENTS

| | | |
|---|---|---|
| WO | WO 92/10971 A1 | 7/1992 |
| WO | WO 95/33506 A1 | 12/1995 |
| WO | WO 98/44854 A1 | 10/1998 |
| WO | WO 98/48706 A1 | 11/1998 |
| WO | WO 98/49191 A1 | 11/1998 |
| WO | WO 99/01076 A1 | 1/1999 |
| WO | WO 99/34741 A1 | 7/1999 |
| WO | WO 99/64109 A1 | 12/1999 |
| WO | WO 00/48510 A1 | 8/2000 |
| WO | WO 00/51510 A1 | 9/2000 |
| WO | WO 00/62699 A2 | 10/2000 |
| WO | WO 01/02042 A1 | 1/2001 |

(56) References Cited

FOREIGN PATENT DOCUMENTS

| WO | WO 01/03642 A1 | 1/2001 |
|---|---|---|
| WO | WO 01/10314 A1 | 2/2001 |
| WO | WO 01/13839 A1 | 3/2001 |
| WO | WO 01/13908 A2 | 3/2001 |

OTHER PUBLICATIONS

Becker, et al., "Lung volumes before and after lung volume reduction surgery" Am. J. Respir. CM. Care Med. (1998) 157:15931599.
Brown, et al. Nonhomogeneous alveolar pressure swings in the presence of airway closure. J Appl Physiol. Sep. 1980;49(3):398-402.
Clark, et al., "Lung volume reduction surgery alters management of pulmonary nodules in patients with severe COPD" Chest (1997) 112(6):1494-1500.
Criner, et al. Effect of lung volume reduction surgery on diaphram strength. Am. J. Res. Crit. Care Med. 1998; 157:1578-1585.
European search report dated May 20, 2008 for EP Application No. 02768834.0.
Harada, et al. Re-expansion of refractory atelectasis using a bronchofiberscope with a balloon cuff Chest. 1983; 84(6):725-728.
International search report dated May 16, 2003 for PCT/US2002/028863.
Japanese office action dated Aug. 4, 2008 for JP Application No. 2003-526351 (with English translation).
Kotloff, et al. Comparison of short-term functional outcomes following unilateral and bilateral lung volume reduction surgery. Chest (1998) 113(4):890-895.
MAQUET Servo Ventilator 300/300A Operating Manual (2000).
Office action dated Apr. 9, 2015 for U.S. Appl. No. 12/108,035.
Office action dated May 18, 2012 for U.S. Appl. No. 12/108,035.
Office action dated Jun. 4, 2013 for U.S. Appl. No. 12/108,035.
Office action dated Jun. 17, 2014 for U.S. Appl. No. 12/108,035.
Office action dated Nov. 16, 2011 for U.S. Appl. No. 12/108,035.
Office action dated Dec. 26, 2013 for U.S. Appl. No. 12/108,035.
Rossing. Airflow resistance in lower airway of the dog. Journal of Applied Physiology. 1962; 17(6):977-884.
Sclafani. "Clearing the airways" AARC Times (Jan. 1999) pp. 69-71, 97.
Vieira, et al. A scanographic assessment of pulmonary morphology in acute lung injury. Significance of the lower inflection point detected on the lung pressure-volume curve. Am J Respir Crit Care Med. May 1999;159(5 Pt 1):1612-23.
Informed Plus, document No. 7422. Endotracheal Tube choice, correction dated Nov. 19, 2001. www.ices.on.ca/informed/periodical/subissue/133-ip7422.pdf web page printed Sep. 24, 2007.
Office action dated Jan. 13, 2012 for U.S. Appl. No. 10/241,733.
Office action dated Feb. 14, 2007 for U.S. Appl. No. 10/241,733.
Office action dated Apr. 2, 2008 for U.S. Appl. No. 10/241,733.
Office action dated Apr. 6, 2009 for U.S. Appl. No. 10/241,733.
Office action dated Jun. 4, 2014 for U.S. Appl. No. 10/241,733.
Office action dated Jun. 17, 2011 for U.S. Appl. No. 10/241,733.
Office action dated Aug. 25, 2006 for U.S. Appl. No. 10/241,733.
Office action dated Oct. 2, 2013 for U.S. Appl. No. 10/241,733.
Office action dated Oct. 16, 2007 for U.S. Appl. No. 10/241,733.
Office action dated Nov. 21, 2008 for U.S. Appl. No. 10/241,733.
Office action dated Dec. 17, 2009 for U.S. Appl. No. 10/241,733.
Office action dated Dec. 19, 2014 for U.S. Appl. No. 10/241,733.
U.S. Appl. No. 15/150,324, filed May 9, 2016, Kotmel et al.
Office Action dated Jul. 3, 2017 for U.S. Appl. No. 15/150,324.

* cited by examiner

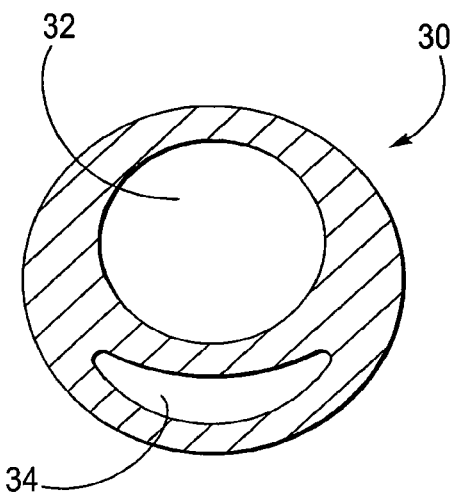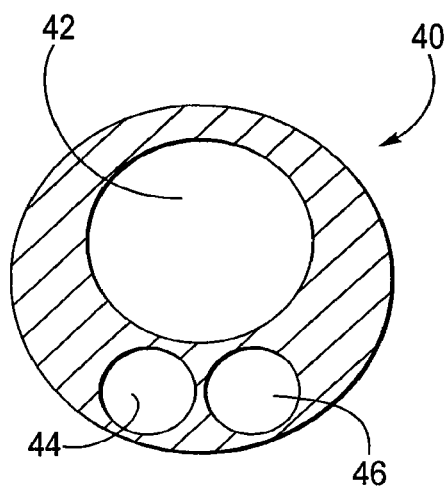
Fig. 6A　　　　　　Fig. 6B
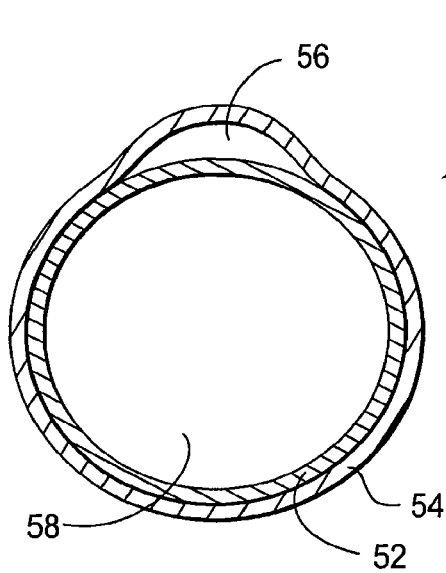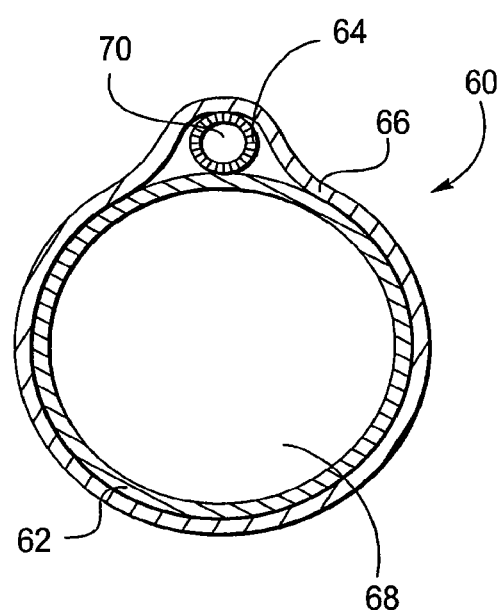
Fig. 6C　　　　　　Fig. 6D

METHOD AND APPARATUS FOR ENDOBRONCHIAL DIAGNOSIS

CROSS-REFERENCES TO RELATED APPLICATIONS

This application is a continuation of U.S. patent application Ser. No. 10/241,733, filed Sep. 10, 2002, which claims benefit, under 37 C.F.R. § 1.78, to U.S. Provisional Patent Application No. 60/318,539, filed Sep. 10, 2001, the complete disclosures of which are incorporated herein by reference.

STATEMENT AS TO RIGHTS TO INVENTIONS MADE UNDER FEDERALLY SPONSORED RESEARCH OR DEVELOPMENT

N/A.

REFERENCE TO A "SEQUENCE LISTING," A TABLE, OR A COMPUTER PROGRAM LISTING APPENDIX SUBMITTED ON A COMPACT DISK

N/A.

BACKGROUND OF THE INVENTION

1. Field of the Invention

The present invention relates generally to medical methods, systems, and kits. Particularly, the present invention relates to methods and apparatus for performing diagnostic testing on individual subsections or segments of a lung. Further, the present invention provides methods and apparatus for more accurate evaluation of the extent and severity of pulmonary disease in the subsections and segments and the effectiveness of various treatment options.

Chronic obstructive pulmonary disease (COPD) is a significant medical problem affecting 16 million people or about 6% of the U.S. population. Specific diseases in this group include chronic bronchitis, asthmatic bronchitis, and emphysema. In general, two types of diagnostic tests are performed on a patient to determine the extent and severity of COPD: 1) imaging tests and 2) functional tests. Imaging tests, such as chest x-rays, CT scans, MRI, perfusion scans, and bronchograms, provide a good indicator of the location, homogeneity and progression of the diseased tissue. However, these test do not give a direct indication of how the disease is affecting the patient's overall lung function and respiration capabilities. This can be measured with functional testing, such as spirometry, plethysmography, oxygen saturation, and oxygen consumption stress testing, to name a few. Together, these diagnostic tests are used to determine the course of treatment for the patient.

Treatment for emphysema may include a variety of options, one such option is Lung Volume Reduction which typically involves resecting diseased portions of the lung. Resection of diseased portions of the lungs both promotes expansion of the non-diseased regions of the lung and decreases the portion of inhaled air which goes into the lungs but is unable to transfer oxygen to the blood. Lung reduction is conventionally performed in open chest or thoracoscopic procedures where the lung is resected, typically using stapling devices having integral cutting blades. While effective in many cases, conventional lung reduction surgery is significantly traumatic to the patient, even when thoracoscopic procedures are employed. Such procedures often result in the unintentional removal of relatively healthy lung tissue or leaving behind of relatively diseased tissue, and frequently result in air leakage or infection. Consequently, alternative therapies have been developed which utilize minimally invasive techniques to isolate target lung tissue segments from other regions of the lung. Isolation is usually achieved by introducing an access catheter endotracheally or thorascopically to the target air passage of the lung. The target lung tissue segment is then collapsed by aspirating air (and any other gases or liquids that may have been introduced) from the segment and optionally sealed off. Exemplary methods and systems to perform such isolation procedures are described U.S. patent application Ser. No. 09/606,320, incorporated herein by reference.

Currently, the diagnostic tests are limited in the amount and type of information that may be generated. For example, diagnostic imaging may provide information to the physician regarding which lung segments "appear" more diseased, but in fact a segment that appears more diseased may actually function better than one that appears less diseased. Functional testing is performed on the lungs as a whole. Thus, the information provided to the physician is generalized to the whole lung and does not provide information about functionality of individual lung segments. Thus, physicians may find difficulty targeting interventional treatments to the segments most in need and to avoid unnecessarily treating segments that are not in need of treatment or less in need. In general, the diseased segments cannot be differentiated, prioritized for treatment or assessed after treatment for level of response to therapy.

For these reasons, it would be desirable to provide systems, methods, devices and kits which would overcome at least some of the shortcomings discussed above. In particular, it would be desirable to provide systems and methods for monitoring, assessing or measuring the functional state of individual lung compartments; such compartments could be an entire lobe, a segment or a subsegment and beyond, hereinafter subsegments and beyond will be referred to simply as segments. It would be further desirable to provide systems and methods of comparing measured data of individual lung compartments to other individual lung compartments and/or to measured data of the lung as a whole. In addition, it would be desirable to provide systems and methods of estimating or predicting the outcome of treatment options prior to actual treatment and also to assess the state of disease and functionality post-treatment. At least some of these objectives will be met by the inventions described hereinafter.

2. Description of the Background Art

Patents and applications relating to lung access, diagnosis, and/or treatment include U.S. Pat. Nos. 6,174,323, 6,083, 255, 5,972,026, 5,752,921; 5,707,352; 5,682,880; 5,660, 175; 5,653,231; 5,645,519; 5,642,730; 5,598,840; 5,499, 625; 5,477,851; 5,361,753; 5,331,947; 5,309,903; 5,285, 778; 5,146,916; 5,143,062; 5,056,529; 4,976,710; 4,955, 375; 4,961,738; 4,958,932; 4,949,716; 4,896,941; 4,862, 874; 4,850,371; 4,846,153; 4,819,664; 4,784,133; 4,742, 819; 4,716,896; 4,567,882; 4,453,545; 4,468,216; 4,327, 721; 4,327,720; 4,041,936; 3,913,568 3,866,599; 3,776,222; 3,677,262; 3,669,098; 3,498,286; 3,322,126; EP 1078601, WO 01/13908, WO 01/13839, WO 01/10314, WO 00/62699, WO 00/51510, WO 00/03642, WO 99/64109, WO 99/34741, WO 99/01076, WO 98/44854, WO 95/33506, and WO 92/10971.

WO 99/01076 describes devices and methods for reducing the size of lung tissue by applying heat energy to shrink collagen in the tissue. In one embodiment, air may be removed from a bleb in the lung to reduce its size. Air passages to the bleb may then be sealed, e.g., by heating, to fix the size of the bleb. WO 98/49191 describes a plug-like device for placement in a lung air passage to isolate a region of lung tissue, where air is not removed from the tissue prior to plugging. WO 98/48706 describes the use of surfactants in lung lavage for treating respiratory distress syndrome.

Lung volume reduction surgery is described in many publications, including Becker et al. (1998) Am. J. Respir. Crit. Care Med. 157:1593-1599; Criner et al. (1998) Am. J. Respir. Crit. Care Med. 157:1578-1585; Kotloff et al. (1998) Chest 113:890-895; and Ojo et al. (1997) Chest 112:1494-1500.

The use of mucolytic agents for clearing lung obstructions is described in Sclafani (1999) AARC Times, January, 69-97. Use of a balloon-cuffed bronchofiberscope to reinflate a lung segment suffering from refractory atelectasis is described in Harada et al. (1983) Chest 84:725-728.

BRIEF SUMMARY OF THE INVENTION

The present invention provides systems, methods, devices and kits for assessing the level of pulmonary disease in individual lung compartments. A lung compartment comprises a subportion of a lung, such as a lobe or a segment, for example. By testing individual lung compartments and determining values of disease parameters reflective of individual subportions or compartments of a lung, the level of disease of the pulmonary system may be more precisely defined. Likewise, compartments may be separately imaged to provide further diagnostic information. Once individual compartments are characterized, they may be compared and ranked based on a number of variables reflecting, for example, level of disease or need for treatment. Such comparison may be aided by simultaneous display of such variables or images on a visual display. Further, the same diagnostic tests may be performed on the lung as a whole or on both lungs and to determine the effect of the diseased lung compartments on the overall lung performance. In addition, the diseased lung compartments may be temporarily isolated and the diagnostic tests performed on the remainder of the lung to determine the affect of the isolation on lung performance. As a result, the most beneficial treatment options may be selected.

In a first aspect of the present invention, a pulmonary diagnostic system is provided comprising an Endobronchial Pulmonary Diagnostic (EPD) device. The EPD device is connectable with a pulmonary catheter configured for introduction into a compartment of a lung. The pulmonary catheter may take a variety of forms, each suitable for acquiring measurement data to characterize the lung compartment or to perform a treatment on the lung compartment. In some cases, such measurement is aided by one or more sensors positioned on the catheter, often near the catheter tip. In a first embodiment, the pulmonary catheter comprises an access catheter. Typical access catheters comprise a catheter body having a relatively large inner diameter to allow sufficient flow of gas or air through the catheter to and/or from the lung compartment. In addition, access catheters often include an occlusion member, such as an inflatable occlusion balloon, near its distal end to seal off the lung passageway around the access catheter leading to the compartment. This provides direct communication with the lung compartment, isolated from the remainder of the lung. In addition, the access catheter may have a number of additional features, such as a guidewire lumen, optical imaging capability and steering capability, to name a few. Additional embodiments of the pulmonary catheter will be described later in conjunction with their use.

As mentioned, a sensor may be disposed on the catheter for generating measurement data reflecting a respiratory feature of the lung compartment. However, such a sensor may be disposed anywhere in the system, including with the EPD device or within connected devices or components. The EPD device typically comprises mechanisms for transferring fluid or gas to or from the lung compartment through the pulmonary catheter. This may be performed to pressurize the lung compartment, a state desired during many testing or measurement procedures. In some embodiments, this mechanisms for transferring may comprise a pump or other driving mechanisms and appropriate tubing or conduits for passage of the fluid or gas. In other embodiments, a pump or other driving mechanisms may be disposed outside of the EPD device. In this case, the mechanisms for transferring the fluid or gas of the EPD device may simply comprise a conduit between the driving mechanisms and the pulmonary catheter.

Generally, the sensors gather measurement data or information which is transmitted to the EPD device. In this case, the EPD device has a mechanisms for receiving the measurement data. Often, the EPD device also comprises mechanisms for processing the measurement data. Processing may comprise converting the measurement data into a form which may be visually displayed, such as in graphs, charts, tables, numbers, images or figures. Or, processing may comprise analyzing the data wherein the data is used to determine or calculate secondary information or data such as an average pressure value, a volume value, a compliance value, an average tidal volume value and/or a resistance value, to name a few. Alternatively, processing may comprise converting the measurement data into a computer readable format. Such conversion may be of the measurement data itself or of secondary data derived from the measurement data.

The processed data is then received by a data receiving component. The receiving component often comprises a visual display. However, the component may alternatively take the form of a computer readable medium, a printer, or a chart recorder, to name a few. The computer readable medium may comprise, for example, disks, diskettes, CD ROMs and tapes.

A variety of measuring components may be used in connection with or disposed within the EPD device. The components include mechanical, electrical, chemical or other means to generate measurement data which characterizes the compartment of the lung which is being measured. For example, a component may include a gas source and a pump which are used to fill the compartment with the gas for pressure or volume measurement. Typically, a component works in conjunction with one or more sensors which are located at any location within the pulmonary diagnostic system. The component may collect data from the sensor and utilize the data in further calculations and measurement functions. Or, the component may simply display the data on a visual display or readout. In any case, the EPD device serves as a central feature of the measurement system, providing user input to control the measurement procedures, coordinating the activities of the measuring components, and transmitting the measurement data between the sensors, for example.

A number of embodiments of the measuring components will be presented. In a first embodiment, the measuring component comprises a pulmonary mechanics unit. The pulmonary mechanics unit is used for measuring a number of variables related to the pulmonary mechanics of the lung compartment. Typically the pulmonary mechanics unit includes mechanisms for generating pressure and volume data of the lung compartment. Pressure is measured by a pressure sensor and volume is derived from measurement by a flow sensor. As mentioned, the sensors may be located near the distal end of the catheter or at any other locations throughout the pulmonary diagnostic system. The pressure and volume data may be plotted on a graph, the pressure data plotted along an x-axis and the volume plotted along a y-axis. The resulting pressure-volume (PV) curve provides information regarding physical characteristics and corresponding level of disease of the lung compartment which is being measured. Based on information provided by the PV curve, the pulmonary mechanics unit or the EPD device may be used to calculate a variety of data values related to the physical characteristics of the lung compartment. For example, the unit or device may include mechanisms for calculating a compliance value for the lung compartment, mechanisms for calculating an average tidal volume value, and mechanisms for calculating a resistance value corresponding to the lung compartment.

In another embodiment the measuring component comprises a physiological testing unit. The physiological testing unit is used for measuring a number of variables related to the physiology of the lung compartment. For example, the physiological testing unit may include mechanisms for measuring ventilation or air flow movement in and out of the lung compartment. In this case the pulmonary catheter may comprise a microcatheter having a velocity sensor mounted on its distal end. After the microcatheter is positioned such that the sensor is located in the passageway entering the compartment to be measured, the velocity sensor measures the movement of airflow into and out of the compartment. Comparison of these values to standard values or values from other compartments in the lung gives an indication of the degree of air trapping or bulk gas exchange in the compartment. Alternatively or in addition, the physiological testing unit may include mechanisms to measure $CO_2$ and/or $O_2$ concentration in the compartment in real time during a breathing cycle to provide an indication of gas exchange. The physiological testing unit may include mechanisms for measuring electrophysiology characteristics of the lung compartment. In one embodiment the mechanisms includes mechanisms for measuring the electrical resistance of the tissue in the compartment and in another embodiment mechanisms includes mechanisms for measuring the electrical activity of the musculature of the tissue in the compartment. Graphical or numerical representation of these values generated by the physiological testing unit or the EPD device may be stored for later use or displayed on the visual display.

In another embodiment, the measuring component comprises a gas dilution unit. The gas dilution unit includes mechanisms for performing Functional Residual Capacity (FRC) testing. FRC testing typically involves introducing a known volume of a noble gas, such as helium, to the lung compartment through, for example, an access catheter. The known volume of noble gas is allowed to mix with the unknown volume of air in the compartment. A sensor then measures the concentration of one of the gases in the system and the volume of air that was initially in the compartment is then calculated. Determining the volume of air initially in the compartment may be useful information used during later treatment.

In some embodiments, the measuring component comprises an imaging unit. The imaging unit may include mechanisms for generating at least one image of a lung compartment. Typically the image includes an X-ray image, a fluoroscopic image, a computed tomography (CT) image, a positron emission tomography (PET) image, a single-photon emission computed tomography (SPECT) image, magnetic resonance image (MRI), or an ultrasonic image. Often traditional external imaging equipment is used while the imaging unit provides, for example, mechanisms for transferring various gases to the lung compartment, including a gas having radiopaque properties, a polarized gas as in the case of MRI, or a liquid as in the case of ultrasonic imaging. Such transfer of gas or liquid may be accomplished with the use of any pulmonary catheter. The resulting images may be individual views of the lung compartment or the views may be combined to generate a composite three-dimensional image of the lung compartment. Alternatively, the views may be of the entire lung minus an isolated compartment or compartments.

In yet another embodiment, the measuring component comprises a mapping unit. The mapping unit is used for determining the position of the pulmonary catheter as it is introduced to the lung and advanced through the bronchial passageways. Due to the multiple branchings of the bronchial anatomy, the position of the catheter within the passageways may be difficult to determine. Thus, the mapping unit can be used to locate the catheter at any time. Often a sensor is mounted on the catheter tip and the unit may include mechanisms for locating the sensor and imaging the position of the sensor within the passageways, reflecting the real time position of the catheter in the lung passageways. Optionally, the sensor may track directional movements. The positioning images may be shown on the visual display for user ease.

As mentioned, the EPD device may be connected with a data receiving component comprising a visual display that is suitable for displaying various acquired data and graphical outputs. It may be appreciated that the information provided by the visual display may be presented in a number of formats and may include a limitless number and type of measurement information. For example, information collected and generated from one or many measuring components may be compiled and displayed on the visual display. Such combination of data may allow the operator or physician to more readily compare information related to various compartments in the lung anatomy, compare data related to an individual patient's lung compartments to other patient's data, compare current measurement data to baseline or previous values, and compare individual compartments to whole lung data. Such display may be graphical, numerical or any other type. The multiple sets of information may be displayed simultaneously or individually, wherein viewing is controlled by the user. Such display may more easily allow the user to rank the compartments in order of level of disease or in order of need for treatment. Likewise, it may be appreciated that images generated from the imaging unit may also be displayed on the visual display.

Once the lung compartments have been sufficiently assessed to determine level of disease, treatment options for the patient may be determined. In some cases, lung volume reduction may be prescribed as the desired treatment protocol. To test the effects of such reduction prior to actual treatment, the lung passageway which leads to the lung compartment to be reduced may be temporarily occluded with a blockage catheter. Typically, the blockage catheter comprises a catheter body having an occlusion member mounted near its distal end. The blockage catheter is advanced through the lung passageways to the compartment that is to be reduced. At this point the lung passageway is occluded by the occlusion member and the lung compartment is effectively isolated from the remainder of the lung. Testing, imaging and evaluation of the overall lung performance may be undertaken to measure the effects of such isolation. This can be performed with multiple permutations of compartments being isolated, either by repositioning the blockage catheter in various passageways or introducing a blockage catheter configured to block numerous passageways at once. If such effects are satisfactory, the physician may choose to reduce the targeted compartment(s) as the treatment option. This technique of temporary occlusion with a blockage catheter may also be employed as a stand alone diagnostic tool wherein a compartment or compartments are isolated and the remainder of the lung is functionally measured or imaged to assess level of disease.

Finally, the measuring component may comprise a treatment unit. The treatment unit is used to perform a lung volume reduction procedure on a lung compartment or any other treatment option. Minimally invasive lung volume reduction typically involves aspirating the contents of the compartment after isolating the compartment from the remainder of the anatomy. This is typically achieved with the use of the an access catheter introduced endotracheally to the target compartment. Once in position, the compartment is isolated by occluding the air passageway, typically by inflating an occlusion balloon mounted on the access catheter. The target compartment is then collapsed by aspirating air and any other gases or liquids that may have been introduced, from the compartment, typically through a lumen in the access catheter. The passageway may then be sealed, for example by deploying a plug within the air passageway.

In a third aspect of the present invention, methods are provided for assessing a lung compartment. Providing a pulmonary diagnostic system as described above, including an EPD device and at least one measuring component connected with the device, a pulmonary catheter is connected to the EPD device for introduction into the lung anatomy of the patient. The distal end of the catheter is introduced through the bronchial passageways of the lung to the compartment of the lung to be measured. Measurement data is generated characterizing the compartment of the lung with the use of the pulmonary diagnostic system. Any of the above described measuring components and/or pulmonary catheters may be used to generate such measurement data. As previously described in relation to each of the components, the generated information and images may be displayed on the visual display. The pulmonary catheter may then be repositioned to another compartment of the lung and measurement data characterizing the other compartment of the lung may then be generated using the pulmonary diagnostic system. As before, the data and/or images may be displayed on the visual display unit. Further, data characterizing the compartment and the other compartments may be simultaneously displayed on the visual display. These steps may be repeated for any number of compartments in the patient's lung and the results may be simultaneously or individually displayed for comparison purposes. Methods may further include ranking the compartments based on level of disease or need for treatment.

If treatment is desired at one or more locations, the effects of treatment may be determined prior to actual treatment. To accomplish this, a blockage catheter may be introduced to the compartment or compartments targeted for possible treatment. The compartment is then isolated from the remainder of the lung by occluding the lung passageway leading to the compartment with an occlusion member on the blockage catheter. A pulmonary catheter may then be positioned or repositioned in a lung passageway leading to the whole lung or a portion of the lung having the isolated compartment within. The pulmonary catheter may then be used to generate measurement data characterizing the whole lung (or portion having the isolated compartment therein) with the use of the pulmonary diagnostic system. It may be appreciated that conventional measurement systems, such as CT or plethysmography, can alternatively be used with the blockage catheter in place to generate such data. If the generated measurement data reflects improved pulmonary function, the isolated compartment may then be reduced by any method. Such treatment may be performed with the use of the pulmonary diagnostic system, specifically with the use of the treatment unit.

In a fourth aspect of the present invention, the methods and devices may be provided in one or more kits. The kits may include a pulmonary diagnostic system comprising an EPD device and optionally at least one measuring component connectable with the device. In addition, the kit shall include instructions for use, setting forth methods according to the present invention. For example, such methods may include connecting a pulmonary catheter to the EPD device, introducing the distal end of the catheter to a compartment of a lung and generating measurement data characterizing the compartment of the lung with the use of the pulmonary diagnostic system. Such kits may further include any of the other system components described in relation to the present invention, any of the other materials or items relevant to the present invention.

Other objects and advantages of the present invention will become apparent from the detailed description to follow, together with the accompanying drawings.

BRIEF DESCRIPTION OF THE DRAWINGS

FIGS. 6A-6F are schematic cross sectional views of a catheter body of an embodiment of an access catheter.

DETAILED DESCRIPTION OF THE INVENTION

Figure 1:
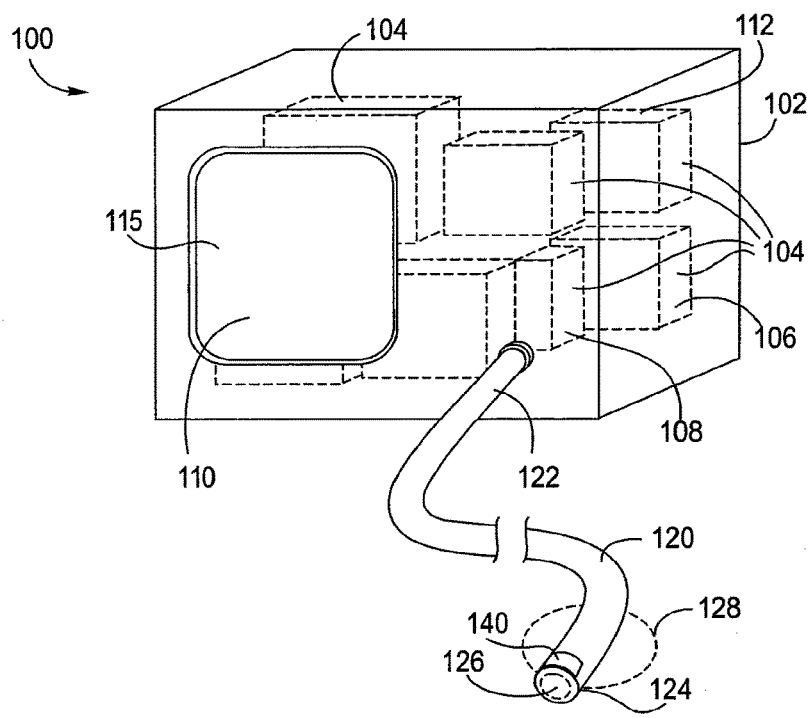
FIG. 1 is a schematic illustration of an EPD device, wherein the measuring components are housed within the EPD device, having a typical pulmonary catheter removably attached.
Figure 2:
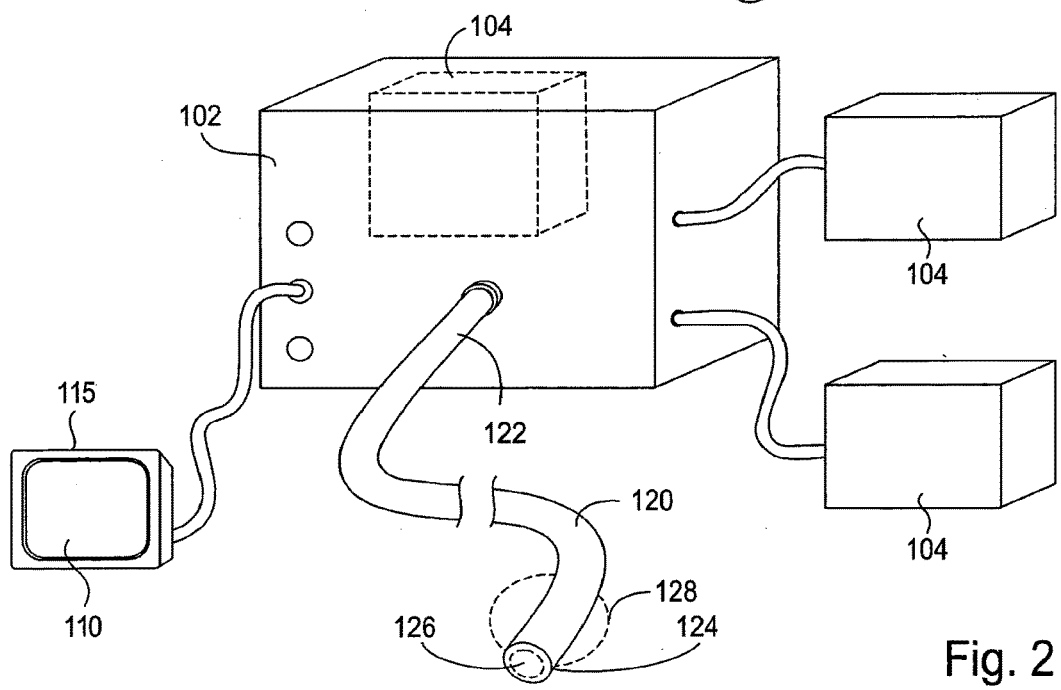
FIG. 2 is a schematic illustration of the EPD device, wherein the measuring components are external and removably attached to the EPD device, having a typical pulmonary catheter removably attached.

The present invention provides for a pulmonary diagnostic system for measuring one or more of a number of parameters related to pulmonary function and/or appearance which may be used in diagnosis, treatment and monitoring or occasional assessment of a patient's disease level. Central to such a system 100 is an Endobronchial Pulmonary Diagnostic (EPD) device 102, as shown in FIGS. 1-2. The EPD device 102 may include a variety of mechanisms and features, which will be described hereinafter, depending on its intended use. The device is connectable with a pulmonary catheter 120, as shown, which is configured for accessing a lung compartment through one or more lung passageways. Here, the catheter 120 is shown as having a proximal end 122, distal end 124, an optional lumen 126 therethrough and an optional occlusion member 128, the lumen 126 and occlusion member 128 shown in dashed-line. A variety of different types of pulmonary catheters 120 may be used, a few embodiments of which will be discussed in later sections.

With the pulmonary catheter 120 positioned in the desired lung passageway, measurement information can be obtained regarding the accessed compartment 154. Typically, this involves the use of at least one sensor. The sensors may include pressure sensors, temperature sensors, air flow sensors, $CO_2$ sensors, $O_2$ sensors, infrared Doppler devices, current or resistivity sensors, laser diode sensors, pulse emitting diode sensors, and/or frequency emitting diodes, to name a few. As shown in FIG. 1, the sensors 140 may be located near the distal end 124 of the catheter 120. Alternatively, the sensors 140 may be located at any point along the catheter 120 or within the EPD device 102 or one or more measuring components 104.

Measuring components 104, shown schematically in FIG. 1 as dashed-lined boxes within the EPD device 102, may take many forms and may perform a variety of functions. For example, the components 104 may include a pulmonary mechanics unit 107, a physiological testing unit 109, a gas dilution unit 106, an imaging unit 108, a mapping unit 112 or a treatment unit 113, to name a few. Embodiments of such components 104 will be discussed in detail in later sections. As illustrated, the components 104 may be integral with or disposed within the EPD device 102. Alternatively, as shown in FIG. 2, some or all of the components 104 may be external to and/or removably connectable with the EPD device 102. In addition, a data receiving component 115 may be integral with, disposed within or removably connectable with the EPD device 102. Here, the data receiving component 115 is shown as a visual display 110. However, the component 115 may alternatively take the form of a computer readable medium, a printer, or a chart recorder, to name a few.

Figure 3:
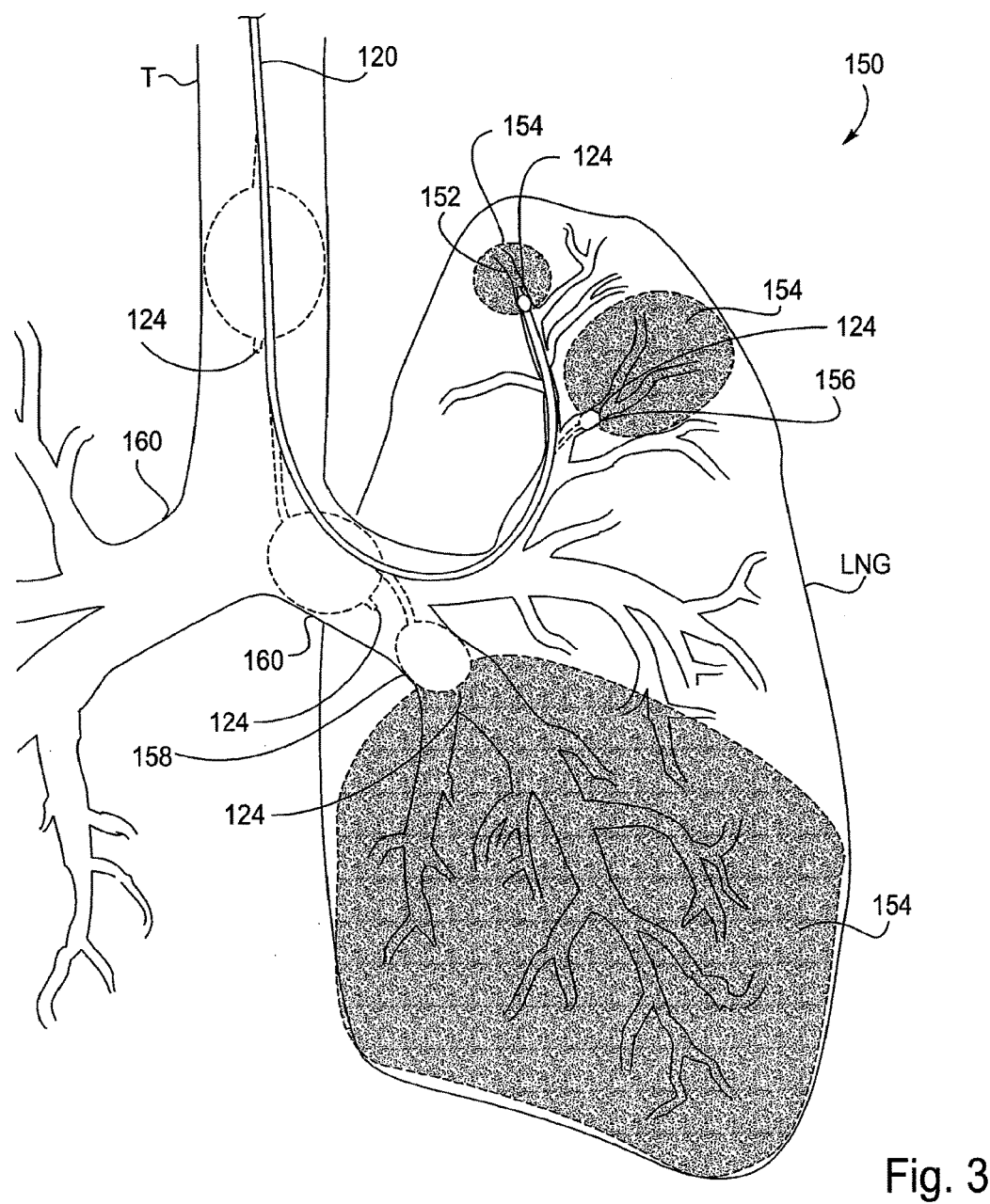
FIG. 3 illustrates a patient's lung wherein the pulmonary catheter is introduced to various locations in the bronchial tree isolating a variety of different sized lung compartments for diagnosis and/or treatment.

As illustrated in FIG. 3, the catheter 120 is configured for introduction into the pulmonary anatomy 150, particularly into a bronchial passageway. As shown, the catheter 120 may be introduced into the bronchial passageways of a lung LNG to various depths. For example, as shown in solid line, the catheter 120 may be introduced so that it's distal end 124 is positioned within a distant lung segment 152 of the branching passageways. In this position, the catheter 120 can optionally isolate and measure an individual compartment 154 of the lung LNG, illustrated by a shaded dashed-lined circle. Alternatively, as shown in dashed-line, the distal end 124 may be positioned in a larger lung segment 156 of the branching passageways. In this position, the catheter 120 can measure another individual compartment 154 of the lung LNG, illustrated by a larger shaded dashed-lined circle. Similarly, the distal end 124 may be positioned in an even larger lung segment 158 to measure an even larger compartment 154, such as one or more lobes. By positioning the distal end 124 in a major takeoff branch 160 to the lung LNG, the lung LNG itself can be measured for comparison to the individual compartments. And, by positioning the distal end 124 in the trachea T, above the takeoff branches 160, the both of the lungs can be measured. Thus, it may be appreciated that any testing, imaging or other functions described in relation to a compartment 154 may also be performed on an entire lung LNG or both lungs.

With the pulmonary catheter 120 positioned in the desired lung passageway as described, the isolated compartment 154 can be assessed. In some instances, fluid or gas is transferred to or from the lung compartment through the pulmonary catheter. This may be performed to pressurize the lung compartment, a state desired during many testing or measurement procedures. In some embodiments, the EPD device 102 comprises mechanisms for transferring such fluid or gas. In some instances, this mechanisms for transferring may comprise a pump or other driving mechanisms and appropriate tubing or conduits for passage of the fluid or gas. In other instances, a pump or other driving mechanisms may be disposed outside of the EPD device 102. In this case, the mechanisms for transferring the fluid or gas of the EPD device 102 may simply comprise a conduit between the driving mechanisms and the pulmonary catheter.

Generally, the sensors 140 gather measurement data or information which is transmitted to the EPD device 102. In this case, the EPD device 102 has a mechanisms for receiving the measurement data. Often, the EPD device 102 also comprises mechanisms for processing the measurement data. Processing may comprise converting the measurement data into a form which may be visually displayed, such as in graphs, charts, tables, numbers, images or figures. Or, processing may comprise analyzing the data wherein the data is used to determine or calculate secondary information or data such as an average pressure value, a volume value, a compliance value, an average tidal volume value and/or a resistance value, to name a few. Alternatively, processing may comprise converting the measurement data into a computer readable format. Such conversion may be of the measurement data itself or of secondary data derived from the measurement data.

The processed data is then received by a data receiving component 115. As mentioned, the receiving component 115 often comprises a visual display 110. However, the component 115 may alternatively take the form of a computer readable medium, a printer, or a chart recorder, to name a few. The computer readable medium may comprise, for example, disks, diskettes, CD-ROMs and tapes. In other cases, one or more measuring components 104 receive the processed data. The processed data may then be used in conjunction other mechanisms within the components. For example, a component may perform a testing function while maintaining the lung compartment at a specific level of pressurization. Thus, the component may utilize measurement data from a pressure sensor while performing testing functions.

When more than one measuring component or a measuring component 104 and a data receiving component 115 are included in the pulmonary diagnostic system 100, the EPD device 102 comprises mechanisms for coordinating the functioning of the measuring components, such as the transfer of gas or fluid between the components and the lung compartment, the passage of information or measurement data between the measuring components, between the sensors and the measuring components or between the measuring components and the data receiving components, to name a few. Such control of activities may result from pre-programming, user input or both.

In other embodiments, measurement simply involves one or more measuring components without the use of a sensor. This may be the case in pulmonary imaging in which a component 104 infuses an isolated compartment 154 with an imaging fluid or gas. The lung compartment 154 may be visualized externally, with the use of a fluoroscopy, nuclear, MRI or CT imaging system, or may be visualized with the use of another component 104 within or attached to the EPD device 102. This may also be the case in measuring perfusion parameters. The measurement information is then processed by the EPD device 102 and received by a receiving component 115.

Measurement information for a given lung compartment 154 may be compared with measurement information from one or more other lung compartments 154. For example, information from a distant lung segment may be compared to information from another distant lung segment. By comparing a number of lung segments, the segments can be ranked in terms of level of disease, for example. Or, information from a lobe can be compared with information from a distant lung segment within the lobe. In this way, the affect of the lung segment on overall performance of the lobe can be compared. Further, a lung compartment 154 may be treated, such as by reduction and/or isolation, and remaining areas of the lung or lungs can be measured to determine the effect of the treatment. To determine such effects prior to actual treatment, a blockage catheter may be used which is introduced to a target compartment, the compartment which has been targeted for treatment. With the blockage catheter in place, such treatment is simulated and the effect of the treatment may be determined by measuring the untreated areas, such as a larger compartment which encompasses or contains the target compartment, using, for example, CT imaging or plethysmography. Thus, more effective treatments may be achieved by pinpointing the most efficient compartments to treat.

As mentioned, the above described measurement data or information may be provided to the user in various formats. Typically, such information will be displayed on the visual display 110 in visual form. This may include graphs, charts, tables, number images or figures, to name a few. Alternatively, the data can be recorded in a computer readable format onto computer readable medium, such as diskettes, CD-ROMs, tapes, etc. The data may then be utilized by a computer, a printer, a visual display or any other accessory. In any case, measurement data or information from a number of compartments may be directly compared by simultaneous display of the information from each compartment. Or, multiple imaging views of a compartment may be obtained to establish a three-dimensional composite view of the compartment. In addition, other types of displays may be provided.

As generally described above, the EPD device 102 performs a variety of functions which depend on the elements included in the pulmonary diagnostic system 100 and the functions in which the system 100 is designed to perform. Descriptive embodiments of possible elements comprising the pulmonary diagnostic system 100 are presented below.

Access Catheter

Figure 4:
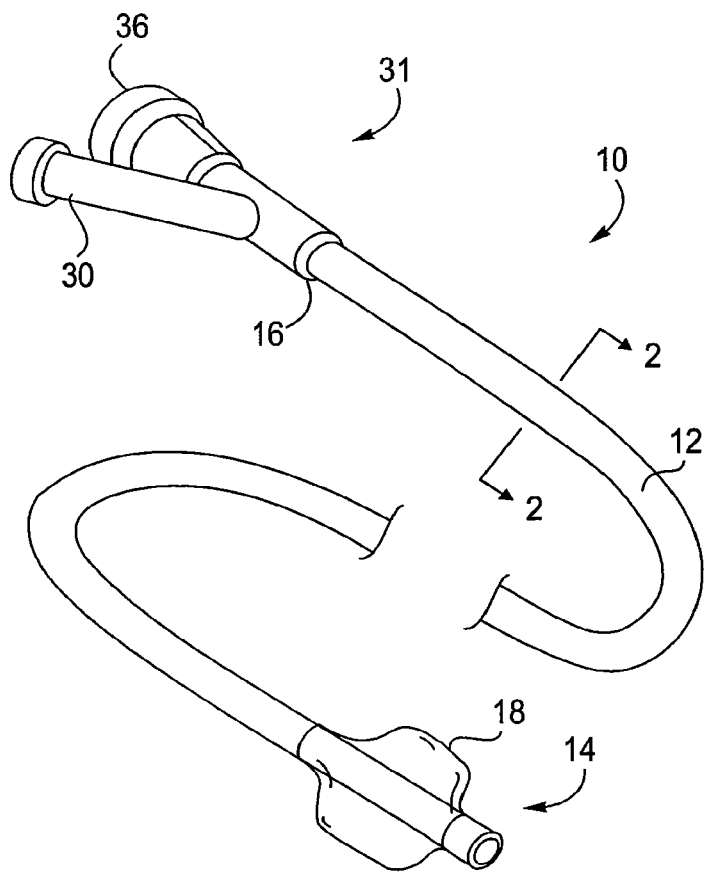
FIGS. 4-5 illustrate a preferred embodiment of an access catheter.
Figure 5:
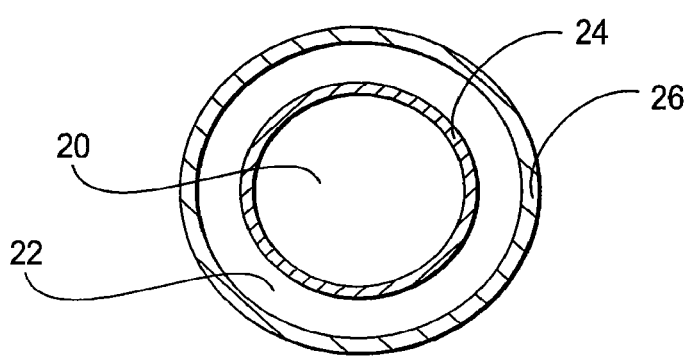

In a number of embodiments, the pulmonary catheter 120 comprises an access catheter 10. An exemplary access catheter 10 is illustrated in FIG. 4 and comprises a catheter body 12 having a distal end 14, a proximal end 16, an inflatable occlusion balloon 18 near its distal end, and at least one lumen therethrough. Usually, the catheter will have at least two lumens, and catheter 10 includes both a central lumen 20 and an annular lumen 22 defined by inner body member 24 and outer body member 26 which is coaxially disposed about the inner body member. The annular lumen 22 opens to port 30 on a proximal hub 31 and provides for inflation of balloon 18. The central lumen 20 opens to port 36 on hub 31 and provides for multiple functions, including optional introduction over a guidewire, aspiration, introduction of secondary catheters, such as sealing catheters, measurement catheters and the like.

Figure 6E:
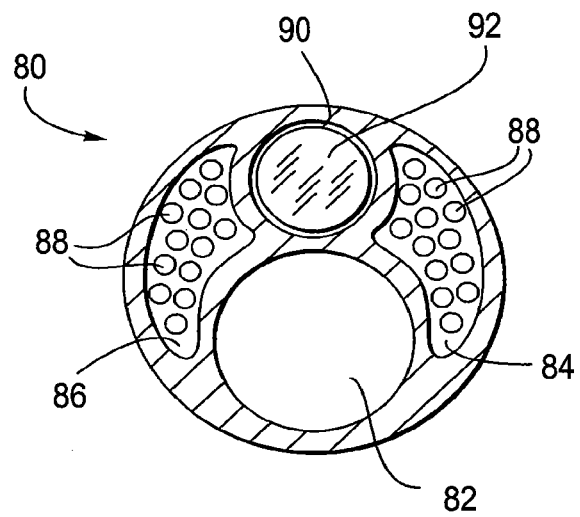

The access catheter 10 may be modified in a number of ways, some of which are illustrated in FIGS. 6A-6F. For example, instead of a inner and outer coaxial tube construction, the catheter can be a single extrusion having a catheter body 30 with a circular main lumen 32 and a crescent-shaped inflation lumen 34, as illustrated in FIG. 6A. Alternatively, shown in FIG. 6B, the catheter body 40 may be formed as a single extrusion having three lumens, i.e., a primary lumen 42 for receiving a guidewire, applying aspiration, delivering secondary catheters, and/or other functions. A second lumen 44 can be provided for inflating the occlusion balloon, and a third lumen 46 can be provided as an alternative guidewire or functional lumen. Catheter body 50 comprising a main tubular body 52 having an outer layer 54 fused thereover to define a lumen 56 suitable for balloon inflation as shown in FIG. 6C. A primary lumen 58 is formed within the main tubular member 52. As a slight alternative, catheter body 60 can be formed from a primary tubular member 62, and a secondary tubular member 64, where the tubular members are held together by an outer member 66, such as a layer which is applied by heat shrinking. The primary tubular member 62 provides the main lumen 68 while secondary tube 64 provides a secondary lumen 70. The secondary lumen 70 will typically be used for balloon inflation, while the primary lumen 68 can be used for all other functions of the access catheter.

The dimensions and materials of access catheter 10 are selected to permit endotracheal introduction and intraluminal advancement through the lung bronchus, optionally over a guidewire, and/or through a primary tracheal tube structure and/or inside the working channel of a bronchoscope. Suitable materials include low and high density polyethylenes, polyamides, nylons, PTFE, PEEK, and the like, particularly for the inner tubular member 24. The outer member, including the occlusion balloon, can be made from elastomeric materials, such as polyurethane, low density polyethylene, polyvinylchloride, silicone rubber, latex, and the like. Optionally, portions of the outer tubular member 26 proximal to the inflatable balloon can be made thicker and/or reinforced so that they do not dilate upon pressurization of the balloon. Exemplary dimensions for the access catheter 10 are dependent on its use. A multi-purpose access catheter 10 should have a working lumen, such as a central lumen 20, main lumen 32, primary lumen 42 or similar such lumen, adequately sized for a number of procedures. If the catheter 10 is to be used in procedures such as functional residual capacity testing or the generation of pressure vs. volume curves, the working lumen should be approximately 1.5-3.5 mm ID, assuming a catheter 10 length of approximately 45-80 cm. In other situations, however, the working lumen may be smaller.

Figure 6F:
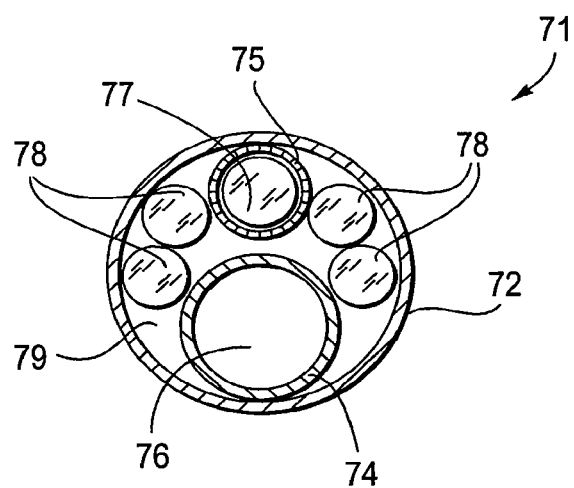

Optionally, the access catheter in the present invention can be provided with optical imaging capability. As shown in FIG. 6E, catheter body 80 can be formed to include four lumens, typically by conventional extrusion processes. Lumen 82 is suitable for passage over a guidewire. Lumens 84 and 86 both contain light fibers 88 for illumination. Lumen 90 carries an optical wave guide or image fiber 92. Lumen 82 can be used for irrigation, aspiration or other functions, typically after the guidewire is withdrawn. Balloon inflation can be effected through the space remaining and lumens 84 and 86 surrounding the light fibers 88. Referring to FIG. 6F, an alternative embodiment of the catheter body 71 is formed as a coaxial arrangement of a number separate tubes. Outer tube 72 contains a separate guidewire tube 74 defining lumen 76 which permits introduction over a guidewire as well as perfusion and aspiration after the guidewire is removed. Second inner tubular member 75 will carry an optical image fiber 77 and a plurality of light fibers 78 are passed within the remaining space 79 within the outer tubular member. In both catheter constructions 80 and 70, forward imaging can be effected by illuminating through the light fibers and detecting an image through a lens at the distal end of the catheter. The image can be displayed on conventional cathode-ray or other types of imaging screens. In particular, forward imaging permits a user to selectively place the guidewire for advancing the catheters through a desired route through the branching bronchus. In some cases in which the working lumen is particularly large, as described above in relation to use in functional residual capacity testing, an alternative cross-sectional design will be implemented to provide the necessary dimensions.

Figure 7:
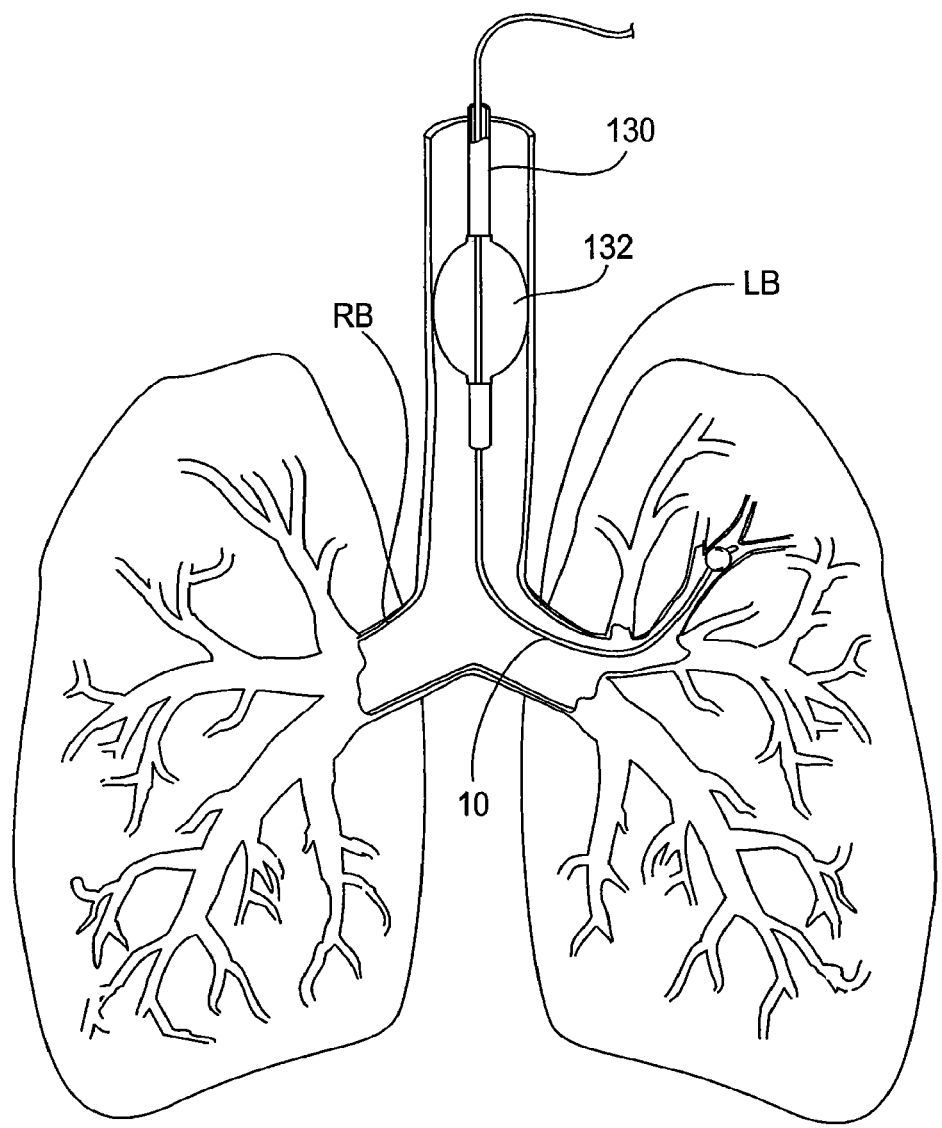
FIG. 7 illustrates a pulmonary catheter introduced through a visualizing endotracheal tube.

As previously described, the catheter 10 can be advanced to a compartment within a lung through a patient's trachea. Advancement through the trachea T is relatively simple and will optionally employ a guidewire to select the advancement route through the branching bronchus. As described above, steering can be effected under real time imaging using the imaging access catheters illustrated in FIGS. 6E-6F. Optionally, the catheter may be inserted through the working channel of a bronchoscope, using the bronchoscope vision for navigation. Or the access catheter 10 may be introduced through a visualizing tracheal tube, such as that described in U.S. Pat. No. 5,285,778, licensed to the assignee of the present application and incorporated by reference for all purposes. As shown in FIG. 7, the visualizing endotracheal tube 130 includes an occlusion cuff 132 which may be inflated within the trachea just above the branch of the left bronchus and right bronchus LB and RB, respectively. The visualizing endotracheal tube 130 includes a forward-viewing optical system, typically including both illumination fibers and an image fiber to permit direct viewing of the main branch between the left bronchus LB and right bronchus RB. Thus, initial placement of access catheter can be made under visualization of the visualizing endotracheal tube 130 and optionally the access catheter 10 itself. The access catheter 10 is advanced until its distal end 14 reaches a region in the bronchus which leads directly into the lung compartment. The access catheter 10 may have elements or accessories for steering and sufficient torque response and pushability to make advancement and navigation through the bronchial tree possible. In addition, the catheter 10 may include positioning sensors so as to determine the location of the catheter with respect to the complete lung anatomy. This will be described in detail in a later section.

In addition, it may be appreciated that the access catheter 10 can be a modular system or a multi-component system. For instance, the access catheter 10 may comprise a viewing scope and a sheath for use with the viewing scope as described in co-pending application Ser. No. 09/699,313, the full disclosure of which is incorporated herein by reference. The viewing scope includes or consists essentially of a flexible elongated body, an optical viewing fiber or video chip, and a light transmitting bundle. The viewing scope may be in the form of conventional bronchoscope or a conventional articulated flexible scope having dimensions suitable for introduction in and through the lung passageways. The sheath comprises a flexible tubular body having a proximal end, a distal end, and at least a first lumen therethrough. The sheath will further comprise an inflatable cuff disposed near its distal end, where the inflatable cuff may be inflated through a lumen which is present in the tubular body itself or formed in a separate inflation tube. The viewing scope is introduced into the lumen of the flexible tubular body of the sheath to form an assembly where a viewing end of the viewing scope is located at the distal end of the sheath. The assembly of the viewing scope and sheath may then be introduced to a lung passageway so that the inflatable cuff lies adjacent to a target location in the passageway. The cuff may then be inflated to temporarily occlude the target location. The sheath may also have additional working channels in order to perform aspects of the diagnostic testing, such as carbon dioxide sensing or polarized gas delivery.

Further, the access catheter 10 may comprise one or more sensors to measure a variety of variables related to pulmonary function. Such sensors will typically be located near the distal end 14 of the catheter 10, however they may be located at any location along the length of the catheter body 12. Individual sensor types will be described in relation to each type of measurement described below.

Pulmonary Mechanics Unit

Figure 8:
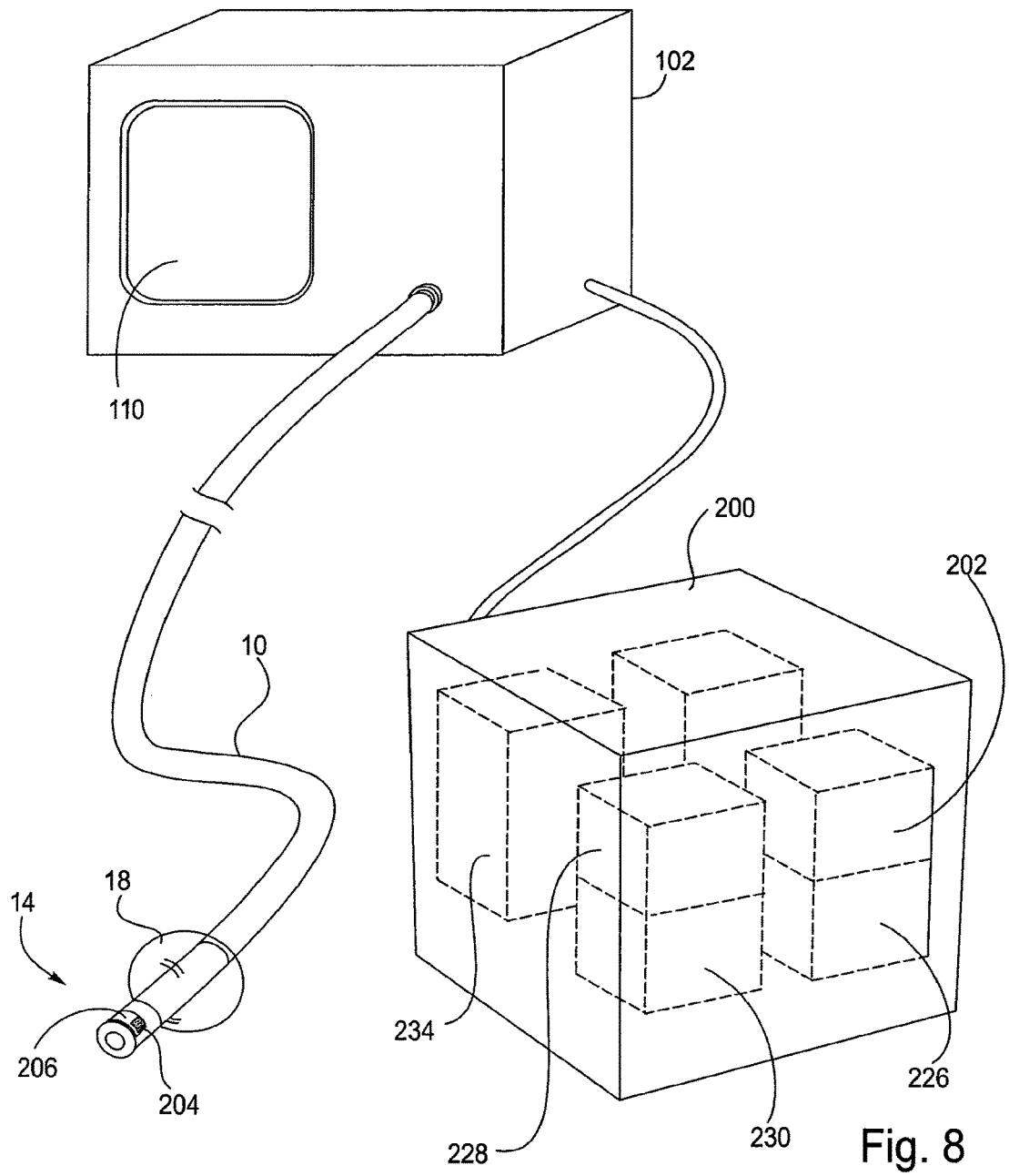
FIG. 8 illustrates an EPD device and a measuring component comprising a pulmonary mechanics unit, wherein an access catheter is attached to the EPD device.

In some embodiments, a measuring component 104 of the pulmonary diagnostic system 100 comprises a pulmonary mechanics unit 200, as shown in FIG. 8. For clarity, the pulmonary mechanics unit 200 is illustrated as a separate attachable unit, however it may be appreciated that the unit 200 may be internal to the EPD device 102. The pulmonary mechanics unit 200 is used for measuring a number of variables related to the pulmonary mechanics of a compartment 154 of a lung LNG.

For example, the pulmonary mechanics unit 200 may include mechanisms 202 for generating pressure and volume data of the lung compartment 154. Generation of such data is achieved by slowly inflating the lung compartment 154 and measuring volume delivered and real-time pressure. The inflation process is performed slowly to minimize the affect of any system resistance on the pressure readings. The inflation medium is delivered to the compartment 154 through an access catheter 10 which is removably attached to the EPD device 102. In this case, the distal end 14 of the catheter 10 is inserted into the lung passageway leading to the compartment 154 to be measured and the balloon 18 is inflated to occlude the passageway. In this way, all inflation medium is delivered to the compartment 154 and cannot escape to other areas of the lung.

Figure 9A:
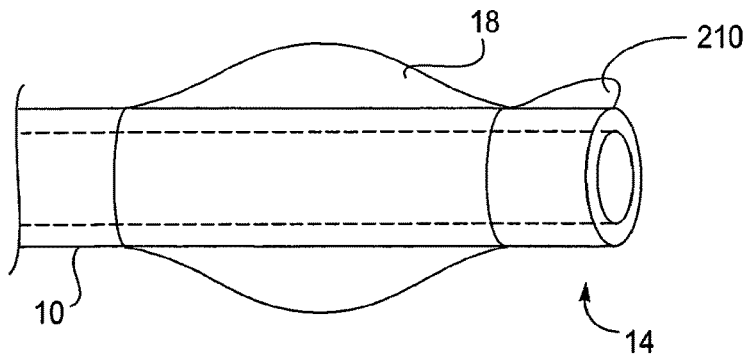
FIGS. 9A-9D illustrate a number of different types of pressure sensors located on an access catheter.
Figure 9B:
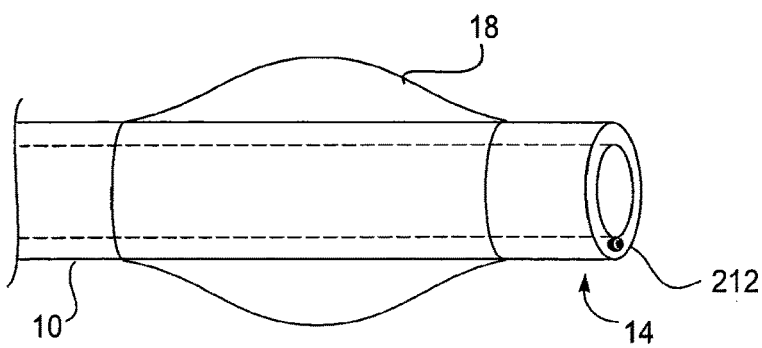
Figure 9C:
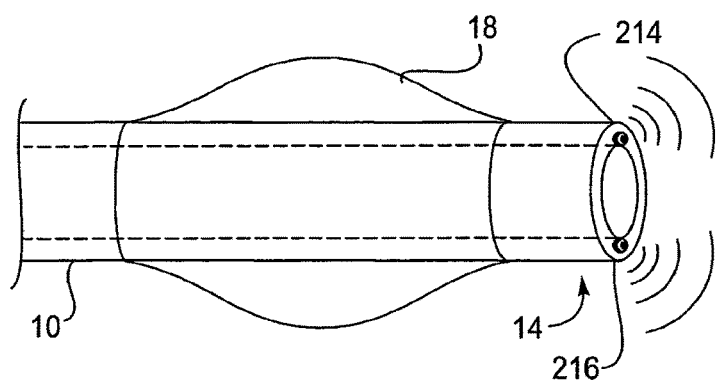
Figure 9D:
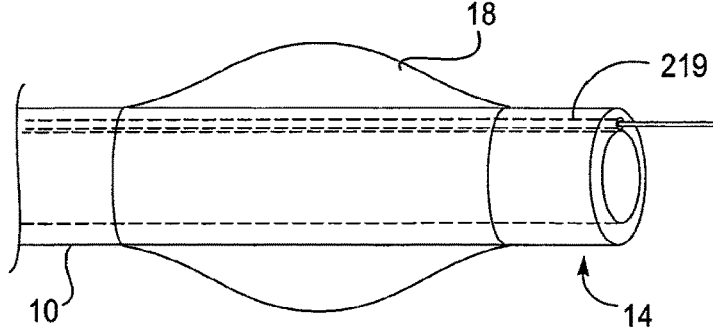

Pressure is measured by a pressure sensor 204 and volume is derived from measurement by a flow sensor 206. As mentioned previously, the sensors 204, 206 may be disposed near the distal end 14 of the catheter 10 or at other locations, including within the EPD device 102 and/or the pulmonary mechanics unit 200. A number of different types of pressure sensors 204 are shown in FIGS. 9A-9D. Referring to FIG. 9A, one embodiment of the pressure sensor 204 comprises a secondary cuff 210 disposed at the distal end 14 of the access catheter 10, distal to the occlusion balloon 18. Another embodiment, shown in FIG. 9B, comprises a Wheatstone bridge, microbellows pressure transducer, or optical fiber 212 imbedded in the wall of the distal end 14. The embodiment of a pressure sensor 204 in FIG. 9C comprises ultrasonic or fiberoptic pressure transducers with a send element 214 and a receive element 216. And the embodiment shown in FIG. 9D comprises a bellows or Wheatstone bridge 218 protruding from a channel 219 in the catheter 10.

Pressurization of the compartment 154 can be performed while the rest of the lung is at an expiratory hold to truly isolate the target compartment and eliminate extraneous events. Alternatively, pressurization can be performed during an inspiratory hold, during regular ventilation or during a pressure hold that is in between end-expiratory pressure and peak inspiratory pressure. These options may provide useful information as to the pulmonary mechanics of the compartment.

Figure 10A:
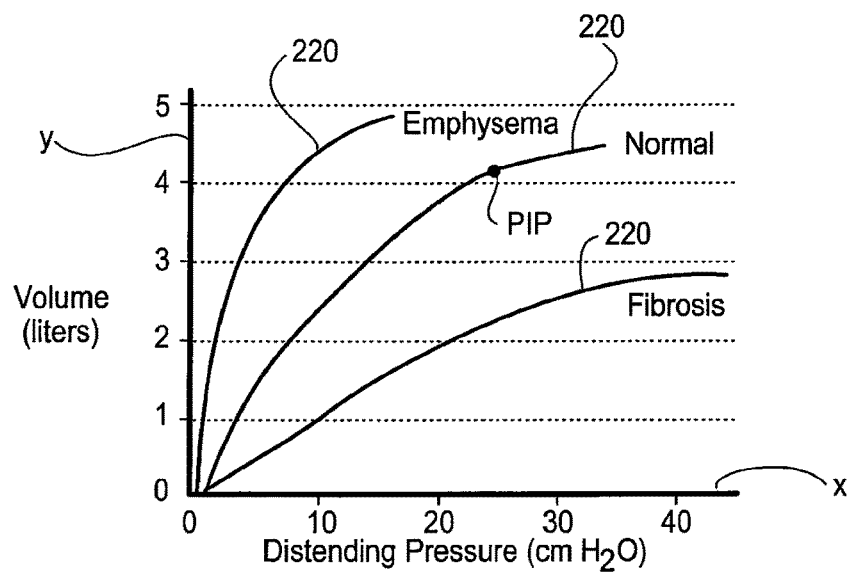
FIG. 10A shows example PV curves plotted on a graph.

Typically, the pressure and volume data is plotted on a graph wherein the pressure data is plotted along an x-axis X and the volume is plotted along a y-axis Y, as illustrated in FIG. 10A. The resulting PV curve 220 provides information regarding the health and level of disease of the compartment 154. FIG. 10A shows three such PV curves 220, the difference in the curves are due to various disease states as stated.

Figure 10B:
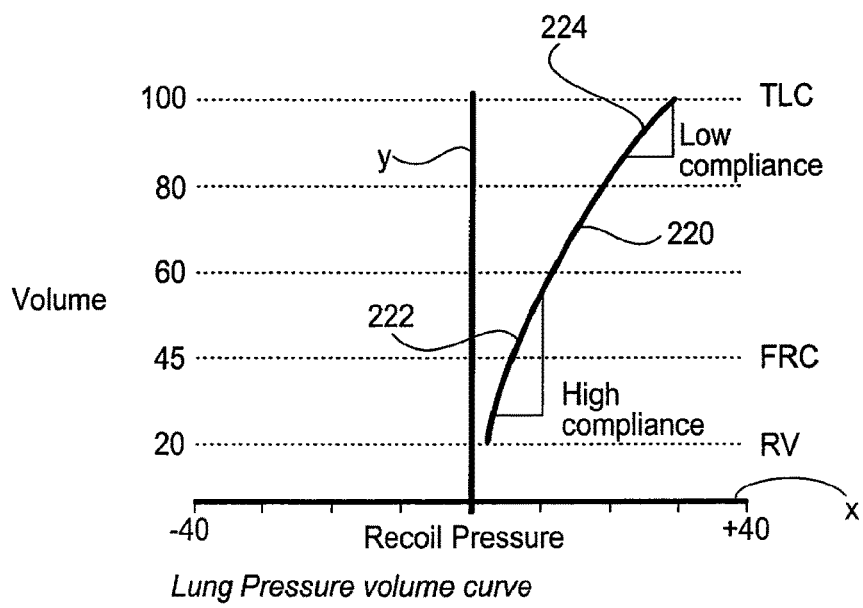
FIG. 10B illustrates regions of various lung compliances along a PV curve.

One type of information which can be derived from a PV curve 220 is compliance. Compliance refers to the distensibility of an elastic structure (such as a lung compartment 154) and is defined as the change in volume of that structure produced by a change in pressure across the structure. In other words, compliance can be defined as the slope of a PV curve 220 at a given point along the curve. As shown in FIG. 10B, in a normal healthy lung compartment at low volume, relatively little positive pressure needs to be applied to increase the volume of the lung quite a bit, as shown by the high compliance area 222. Lung compliance decreases with increasing volume so as the lung compartment is further inflated, more pressure must be applied to get the same increase in volume. This corresponds to the low-compliance area 224. Typically, the compliance will be calculated at an upper inflection point or peak inspiratory pressure PIP, identified in FIG. 10A. Mechanisms 226 for calculating a compliance value from the pressure and volume data is depicted within the pulmonary mechanics unit 200 in FIG. 8, however such mechanisms 226 may alternatively be disposed within the EPD device 102. The PV curves 220 and compliance values will typically be displayed on the visual display 110.

Figure 11:
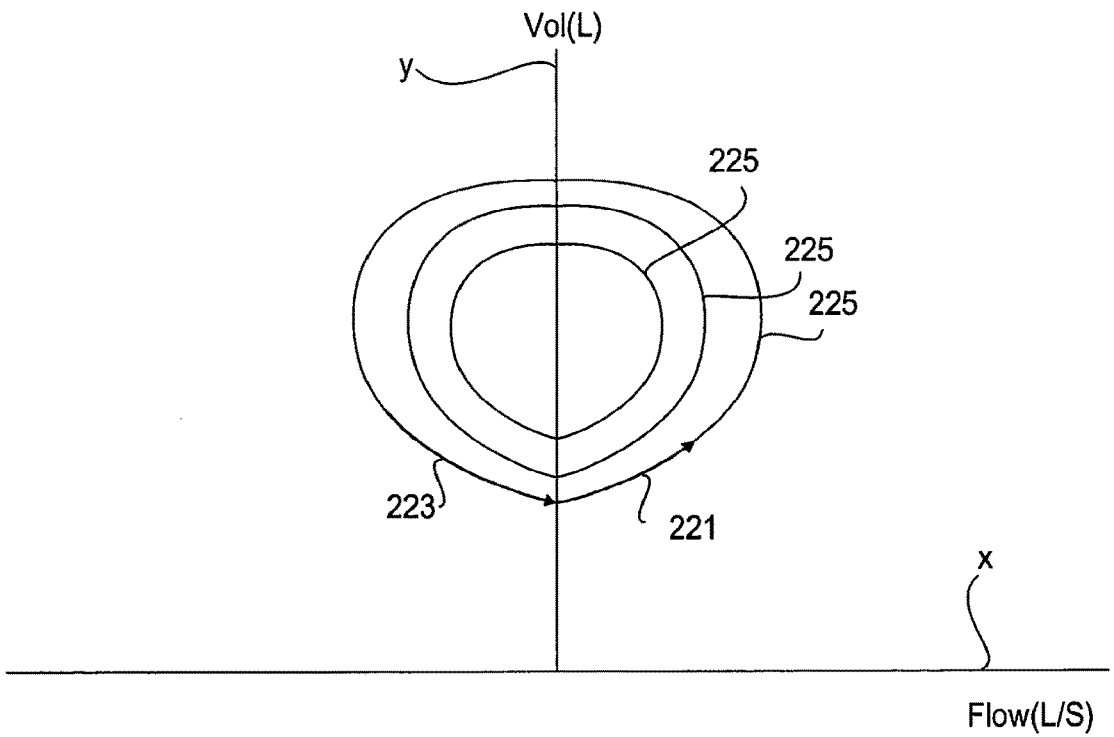
FIG. 11 shows example flow-volume loops plotted on a graph.

Alternatively, volume and flow data may be plotted on a graph as in FIG. 11. Here, flow data is plotted along an x-axis X and volume is plotted along a y-axis Y. During inspiration, volume increases as flow increases and then declines, as indicated by arrow 221. During expiration, volume decreases as flow increases and then declines, as indicated by arrow 223. The resulting trace is a loop 225 indicative of the flow volume characteristics of the compartment 154 accessed. The loop 225 provides information regarding the health and level of disease of the compartment 154. FIG. 11 shows three such loops 225, each corresponding to a different compartment 154 or to the same compartment 154 over time as disease progresses.

Additional respiratory parameters may also be derived from pressure and volume data. For example, the average tidal volume can be measured for a given lung compartment 154. Tidal volume may be described as the volume of air inhaled and exhaled with each breath. Thus, the pulmonary mechanics unit 200 or the EPD device 102 may comprise mechanisms 228 for calculating an average tidal volume value. Here, pressure is set to the PIP and the compartment is ventilated at that pressure. This may be performed while the rest of the lung is in an expiratory hold. Volume is typically measured for three to five breaths over approximately 30 seconds and an average is taken of these values to determine the average tidal volume. In addition, the resistance of a compartment can be derived from pressure and volume data. Resistance may be described as the pressure divided by the volumetric flow rate. In this case, the EPD device 102 or the pulmonary mechanics unit 200 may comprise mechanisms 230 for calculating a resistance value. Further, work of breathing of a compartment can be derived from pressure and volume data. This is done by converting pressure and volume into Joules/liter. The EPD device 102 or the pulmonary mechanics unit 200 may also comprise mechanisms 234 for calculating an average work of breathing value. Graphical or numerical representation of these values may be received by a data receiving component 115 for visual display.

Physiological Testing Unit

In some embodiments, a measuring component 104 comprises a physiological testing unit 300, as shown in FIGS. 12-15. Again, for clarity, the physiological testing unit 300 is illustrated as a separate attachable unit, however it may be appreciated that the unit 300 may be integral or internal to the EPD device 102. The physiological testing unit 300 is used for measuring a number of variables related to the physiology of a compartment 154 of a lung LNG.

Figure 12:
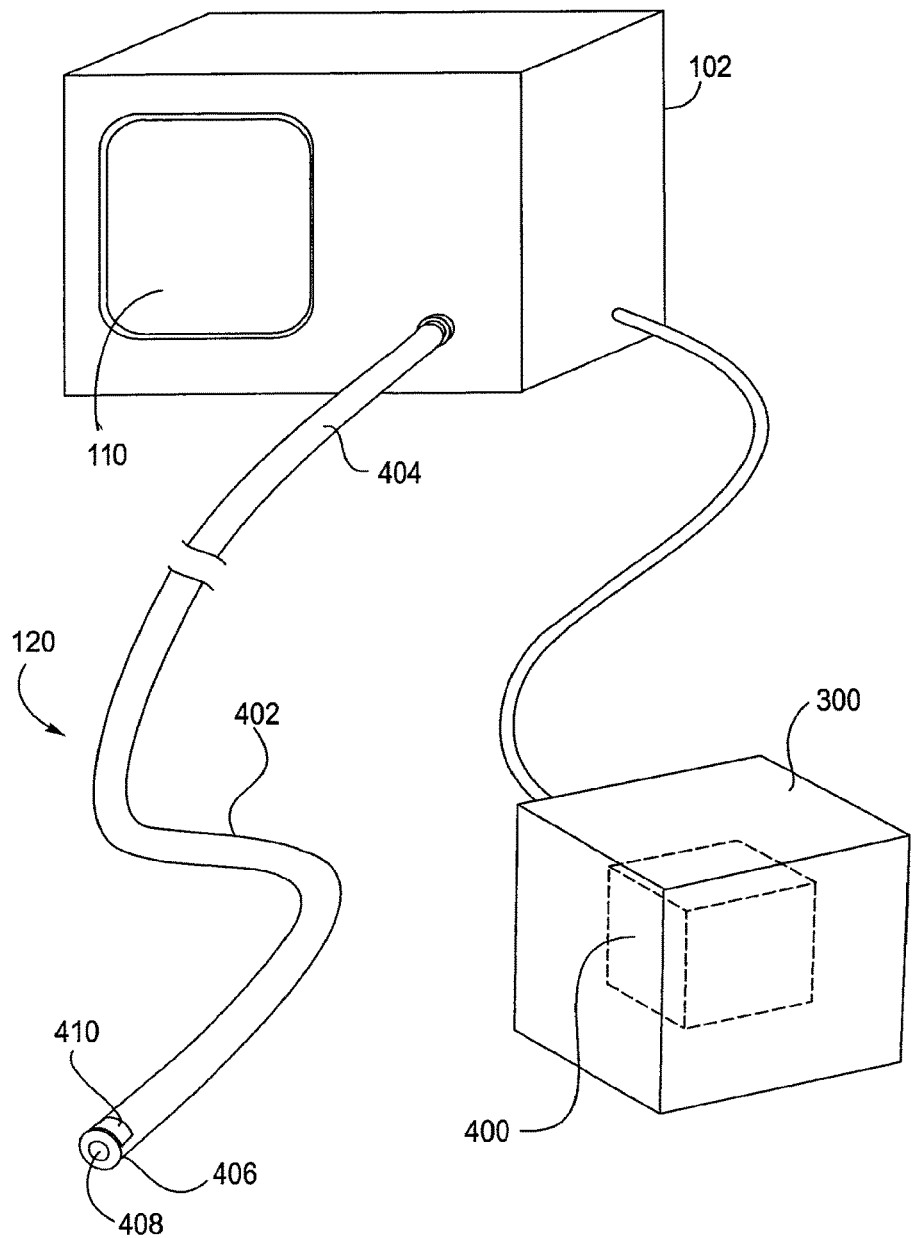
FIG. 12 is a schematic illustration of an EPD device and a measuring component comprising a physiological testing unit. In addition, a microcatheter is shown removably attached to the EPD device.
Figure 12A:
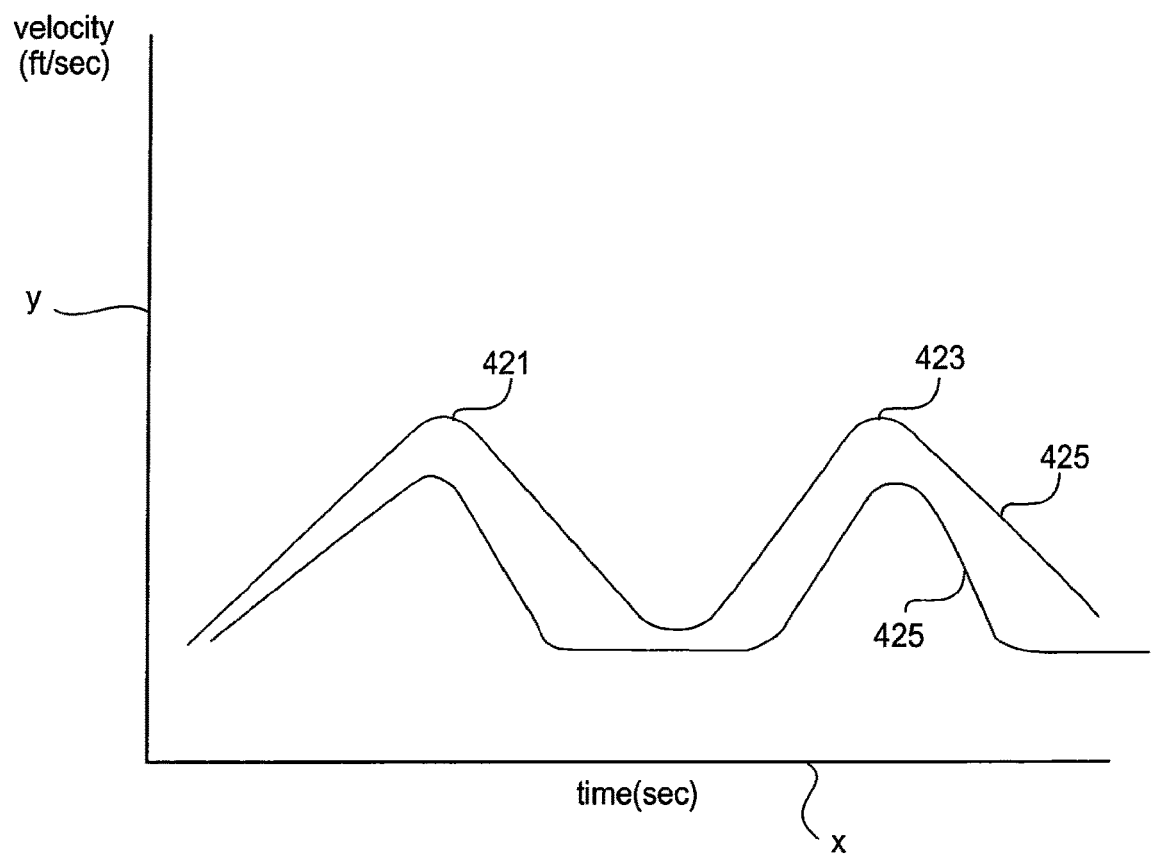
FIG. 12A shows example velocity traces plotted on a graph.

Referring to FIG. 12, the physiological testing unit 300 may include mechanisms 400 for measuring ventilation or velocity of air movement in and out of a compartment 154. Here, the pulmonary catheter 120 comprises a microcatheter 402 having a proximal end 404, a distal end 406, a lumen 408 therethrough and at least one sensor 410 mounted on its distal end 406. The sensor 410 may be a velocity sensor. In this instance, the microcatheter 402 is positioned such that its distal end 406 is entering a compartment 154 to be measured. The microcatheter 402 is sized so that the compartment 154 is not isolated and air movement is not retarded. The velocity sensor 410 measures the velocity of airflow into and out of the compartment 154. Comparison of these values to other compartments gives an indication of the degree of disease of the compartment. For example, as shown in FIG. 12A, velocity versus time data is plotted wherein time is plotted along an x-axis X and velocity is plotted along a y-axis Y. During inspiration, velocity increases to an inspiratory peak 421 and then decreases over time. During expiration, velocity increases to an expiratory peak 423 and then decreases over time. The resulting trace 425 is indicative of the characteristics of the compartment 154 accessed. The trace 425 provides information regarding the health and level of disease of the compartment 154. FIG. 12A shows two such traces 425, each corresponding to a different compartment 154 or to the same compartment 154 over time as disease progresses.

In other embodiments, the sensor 410 may be an oxygen and/or carbon dioxide sensor. When the distal end 406 of the microcatheter 402 is introduced to a lung compartment, the sensor 410 can measure the amount of, for example, carbon dioxide retained in the compartment. Carbon dioxide is indicative of trapped air. Therefore, data derived from such a sensor may provide information as to the level of disease in the compartment. Similarly, a sensor that measures the amount of oxygen retained in the compartment may indicate the level of disease affecting gas transfer through the alveolar sacs. Oxygen sensors can also be used in the performance of oxygen wash-out tests. Here, the air in a lung compartment is replaced as much as possible with 100% oxygen. Then, the decay of oxygen concentration is measured over time using sensor 410. Such decay indicates how well a compartment contributes to ventilation. Further, the ratio of carbon dioxide to oxygen can be determined which is also indicative of disease state.

Figure 13:
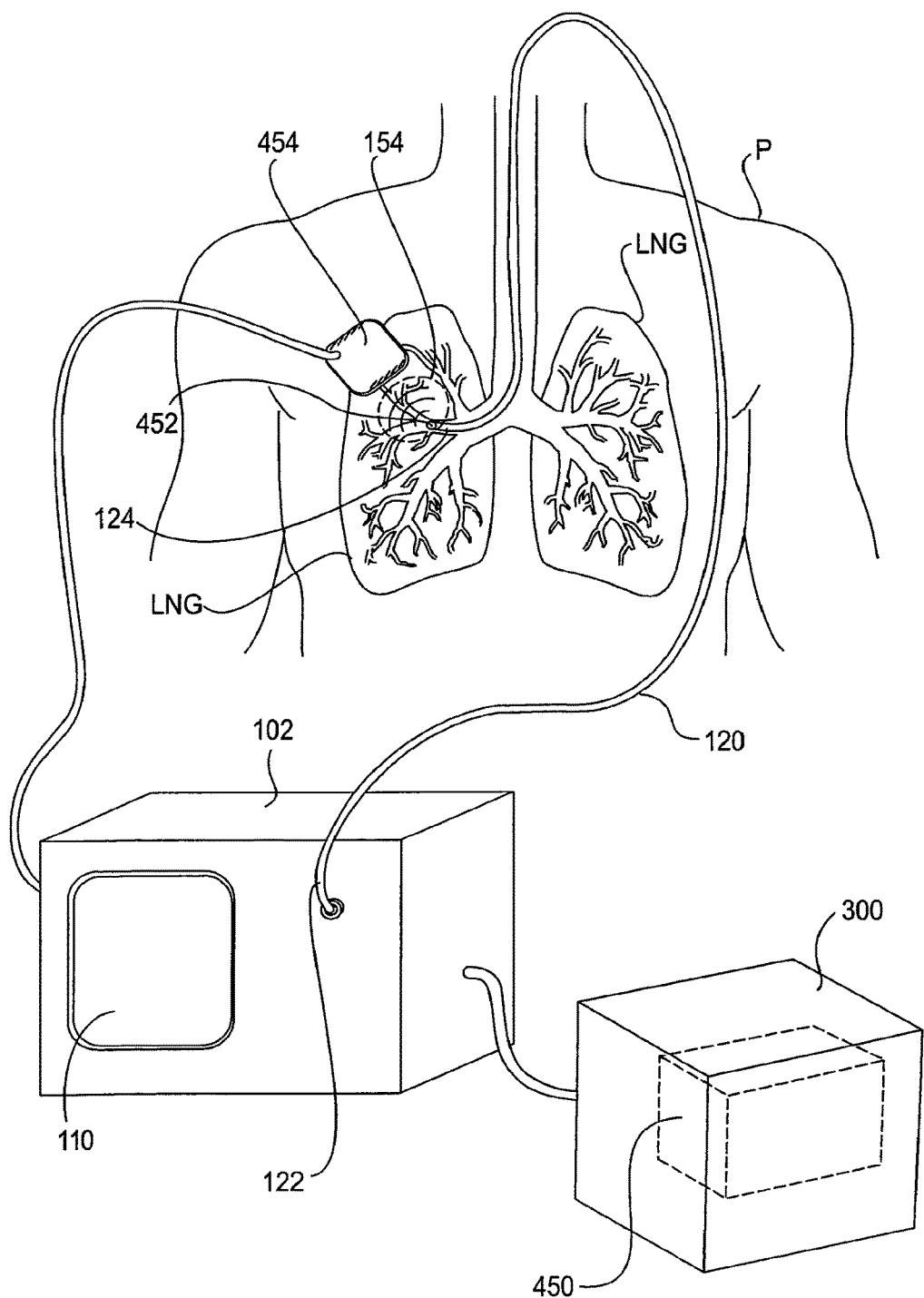
FIG. 13 is a schematic illustration of an EPD device and measuring components comprising physiological testing units which include mechanisms for measuring electrophysiology characteristics of a lung compartment.

Referring to FIG. 13, the physiological testing unit 300 may also include mechanisms 450 for measuring electrophysiology characteristics of a lung compartment 154. In one embodiment, the mechanisms 450 includes measuring the resistance of the tissue in the compartment 154. Here, a pulse emitting sensor 452 is mounted on the distal end 124 of the pulmonary catheter 120. The proximal end 122 of the catheter 120 is removably attached to the EPD device 102 and the distal end 124 is inserted into a lung compartment 154. A receiver 454 is positioned at a second location, for example on the outside of the patient P, and is connected to the EPD device 102. A pulse is emitted from the sensor 452 and a signal is measured by the receiver 454. The signal determines the resistance of the tissue and therefore the state of the disease. For example, diseased tissue will have a different conductivity because of the breakdown of elasticity and/or because of edema/inflammation of the tissue.

In another embodiment, the mechanisms 450 for measuring electrophysiology characteristics of a lung compartment 154 includes measuring the electrical activity of the musculature of the tissue in the compartment 154. Here, two or more leads are mounted on the pulmonary catheter. The leads measure a characteristic voltage signal of the tissue which determines the state of the disease. For example, diseased tissue will have weaker signals due to the breakdown of elasticity.

In another embodiment, the sensor 410 is an infrared sensor which is positioned against the bronchial tissue and a venous oxygen saturation measurement is made. Because blood perfusing diseased lung compartments will have lower oxygenation, disease level can be determined.

Graphical or numerical representation of these values generated by the EPD device 102 or physiological testing unit 300 may be displayed on the visual display 110.

Gas Dilution Unit

Figure 14:
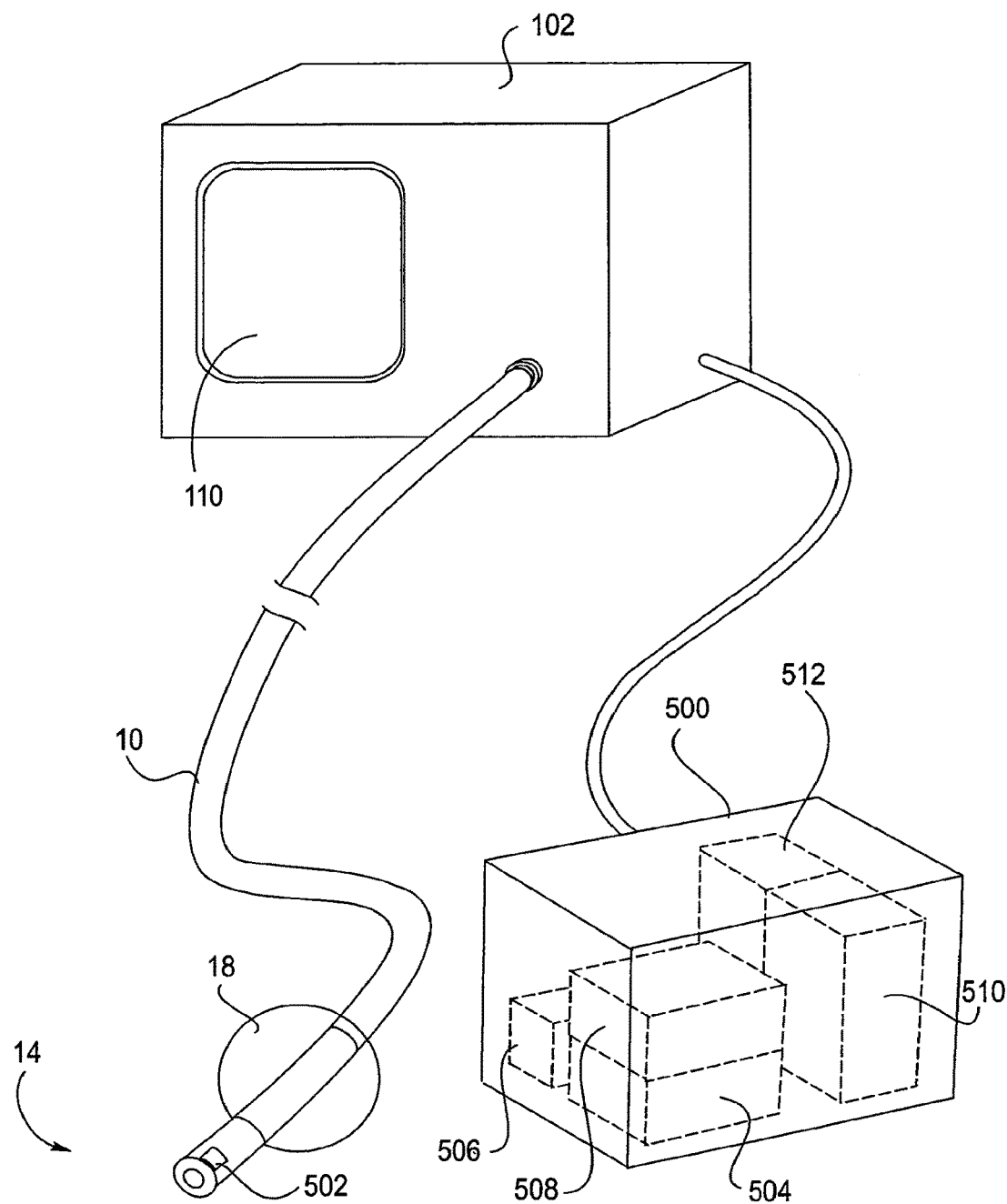
FIG. 14 is a schematic illustration of an EPD device and a measuring component comprising a gas dilution unit, wherein a pulmonary catheter is shown attached to the EPD device.

In some embodiments, a measuring component 104 of the pulmonary diagnostic system 100 comprises a gas dilution unit 500, as shown in FIG. 14. Again, for clarity, the gas dilution unit 500 is illustrated as a separate attachable unit, however it may be appreciated that the unit 500 may be internal to the EPD device 102. The gas dilution unit 500 is used primarily for Functional Residual Capacity (FRC) testing and/or residual volume (RV) testing of a compartment 154 of a lung LNG, since these parameters reflect level of disease.

Typically, the access catheter 10 is used as the pulmonary catheter 120 attached to the EPD device 102, as shown. After the distal end 14 of the catheter 10 is inserted in a lung compartment 154 and the lung passageway is occluded by the balloon 18, the compartment 154 is inflated to the PIP, as previously determined by the mechanisms 202 for generating pressure and volume data. This can be achieved by the pulmonary mechanics unit 200, if available, or it may be achieved by mechanisms 504 for generating pressure and volume data within the gas dilution unit 500 or the EPD device 102. Then, a known volume of a noble gas, such as helium, is introduced from a source of noble gas 506 to the compartment 154 through the access catheter 10. The known volume of noble gas is allowed to mix with the unknown volume of air in the compartment 154 (at PIP). Thorough mixing is accomplished by using a pump 508 that moves gas back and forth through the access catheter 10 in an oscillatory motion. Due to the low volume of the access catheter 10 compared to that of the compartment 154, complete mixing should be accomplished in approximately 1-5 minutes, depending on the mixing efficiency of the incoming noble gas.

A sensor 502 measures the concentration of one of the gases in the system. In some embodiments, the sensor 502 is mounted on the distal end 14 of the catheter 10 as shown. The sensor 502 may be any of the following: a membrane chemical transfer sensor, a photochemical reaction sensor, an electropotential sensor, a microchip, a laser diode, an optical transmittance sensor, or a piezoelectric sensor. When the concentration of this measured gas equilibrates, simple volume mixing laws are used to calculate the volume of air that was initially in the compartment. Thus, the gas dilution unit 500 or EPD device 102 may include mechanisms 510 for determining the concentration of a gas, such as helium, in the system and mechanisms 512 for calculating the initial volume of air in a lung compartment. Determining the volume of air initially in the compartment may be useful information used during later treatment. For example, the compartment may be treated by aspirating trapped air in the compartment. By comparing the measured volume of air aspirated with the calculated initial volume of air in the compartment, the effectiveness of the treatment may be determined.

Imaging Unit

Figure 15:
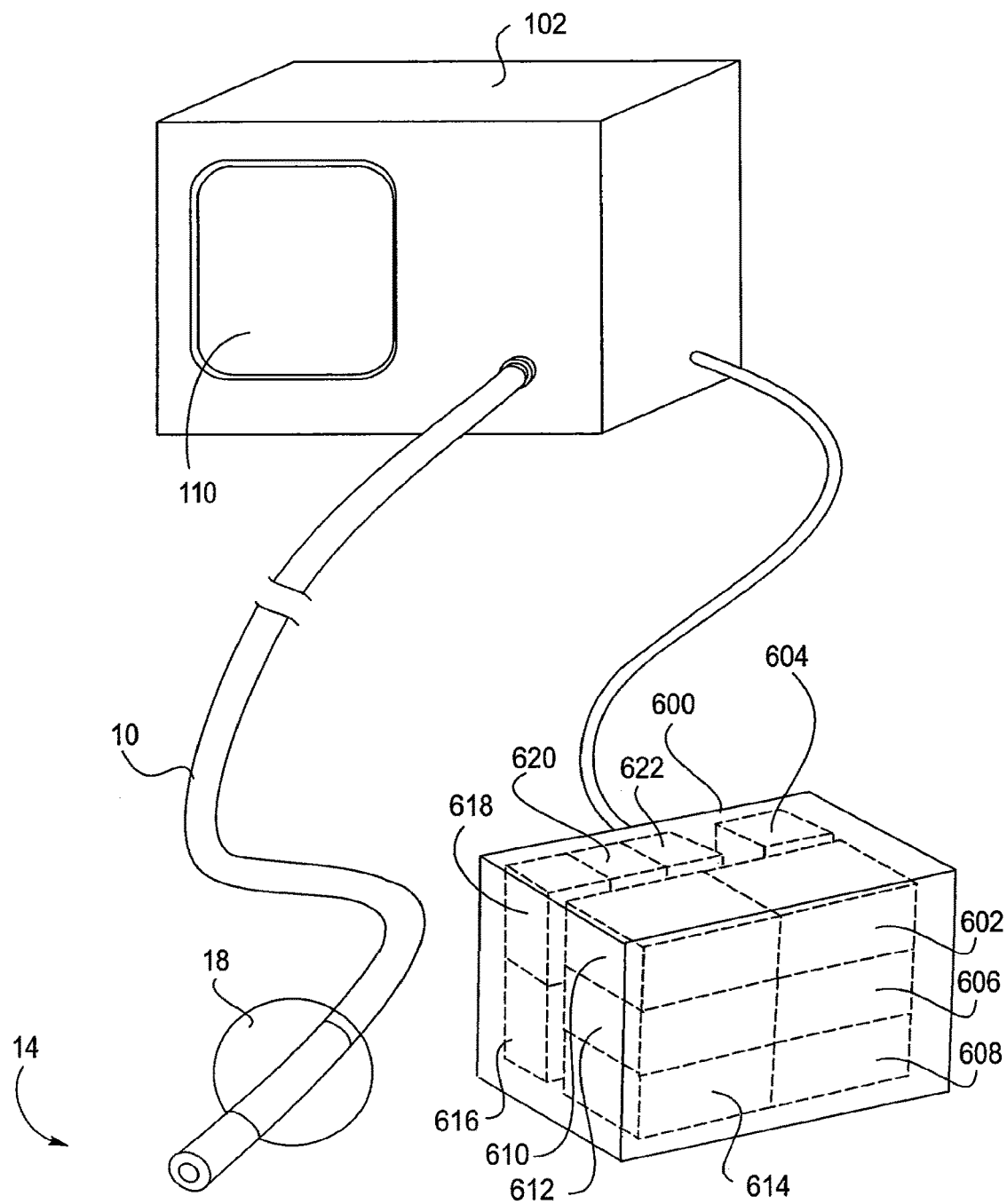
FIG. 15 is a schematic illustration of an EPD device and a measuring component comprising an imaging unit, wherein a pulmonary catheter is shown attached to the EPD device.

In some embodiments, a measuring component 104 of the pulmonary diagnostic system comprises an imaging unit 600, as shown in FIG. 15. Again, for clarity, the imaging unit 600 is illustrated as a separate attachable unit, however it may be appreciated that the unit 600 may be integral or internal to the EPD device 102. The imaging unit 600 is used for generating or assisting in the generation of two-dimensional or three-dimensional images of a compartment 154 of a lung LNG. Often traditional external imaging equipment is used to generate the images while the imaging unit 600 assists in the visualization of individual compartments, as will be described below. In this case, the imaging unit 600 may also serve to transmit and optionally manipulate the images for display in the visual display 110.

Referring to FIG. 15, the access catheter 10 is typically used as the pulmonary catheter 120 attached to the EPD device 102, as shown. After the distal end 14 of the catheter 10 is inserted in a lung compartment 154 the compartment may be visualized by imaging. Such imaging may be enhanced by occluding the lung passageway with the balloon 18 prior to visualization. The imaging unit 600 may include mechanisms 602 for transferring a fluid or gas having radiopaque properties to the lung compartment 154. Such a fluid or gas may be radiopaque or be labeled with radiopaque markers, for example. The compartment 154 is inflated with the fluid or gas to the PIP, as previously determined by the mechanisms 202 for generating pressure and volume data. This can be achieved by the pulmonary mechanics unit 200 or EPD device 102, if available, or it may be achieved by mechanisms 604 for generating pressure and volume data within the imaging unit 600. The imaging unit 600 may further include mechanisms 606 for generating an ultrasound or MRI image of the lung compartment 154. Or, an image may be taken with equipment external to the pulmonary diagnostic system 100 using CT, MRI, PET, x-ray, ultrasound, fluoroscopy or a perfusion scan. While the compartment is filled with an imaging gas or fluid as described above, the remainder of the lung may be filled with a gas or fluid having a stronger or weaker imaging capability. For example, the lung compartment may be filled with a radiopaque gas and the remainder of the lung filled with a weaker concentration of radiopaque gas. As a result, the complete lung will be visible under fluoroscopy with the lung compartment "highlighted" by the stronger concentration of radiopaque gas. It may be appreciated that the concentrations may be reversed wherein the lung is filled with a gas or fluid having a higher concentration than the lung compartment and the lung compartment is highlighted by the weaker concentration of radiopaque gas. Similarly, an individual lung compartment may be blocked or isolated and the remainder of the lung imaged by the methods described above. In any case, the individual compartments may be evaluated which may provide information as to its level of disease.

Multiple images of the lung compartment 154 may be generated, each image having a different view. This may be achieved externally or by mechanisms 608 for generating multiple images. Mechanisms 610 for generating a three-dimensional composite image of the compartment 154 from the individual views may also be included in the imaging unit 600 or the EPD device 102. Alternatively, multiple images of the lung compartment 154 may be generated so that a three-dimensional image is obtained by combining image "slices" of the compartment. This may provide even more diagnostic information regarding the status of the compartment and its level of disease.

Alternatively or in addition, the imaging unit 600 may include mechanisms 612 for transferring a polarized gas to the lung compartment 154. Again, the compartment 154 is inflated with the gas to the PIP, either with the mechanisms 202 or the mechanisms 604 for generating pressure and volume data. The imaging unit 600 may further include mechanisms 614 for generating at least one magnetic resonance image (MRI) of the lung compartment 154. Or, an image may be taken with external MRI equipment. In either case, the anatomy of the compartment may be visualized which may provide information as to its level of disease. Additionally, the imaging unit 600 may further include mechanisms 616 for generating multiple magnetic resonance images of the lung compartment 154 and mechanisms 618 for generating a three-dimensional composite image of the compartment 154. It may be appreciated that some of these mechanisms may be included in the EPD device 102. These images may provide even more diagnostic information regarding the status the compartment and its level of disease.

Alternatively or in addition, the imaging unit 600 may include mechanisms 620 for transferring a liquid such as perfluroban to the lung compartment 154. The imaging unit 600 may further include mechanisms 622 for generating an ultrasonic image of the lung compartment 154. Or, an image may be taken with external ultrasound equipment. In either case, the anatomy of the compartment may be visualized which may provide information as to its level of disease.

It may be appreciated that imaging may be undertaken with the use of any contrast media appropriate for the imaging technique. In addition, such imaging may be performed at different points in the breathing cycle, such as at the end of normal inspiration and exhalation and/or at the end of forced inspiration and exhalation. These images can then be used to calculate lung volumes relevant to disease, such as residual volume (RV), total lung capacity (TLC) and RV/TLC. In addition, imaging may be performed on any number of lung compartments and imaging results may be compared for diagnostic or other purposes.

Mapping Unit

Figure 16:
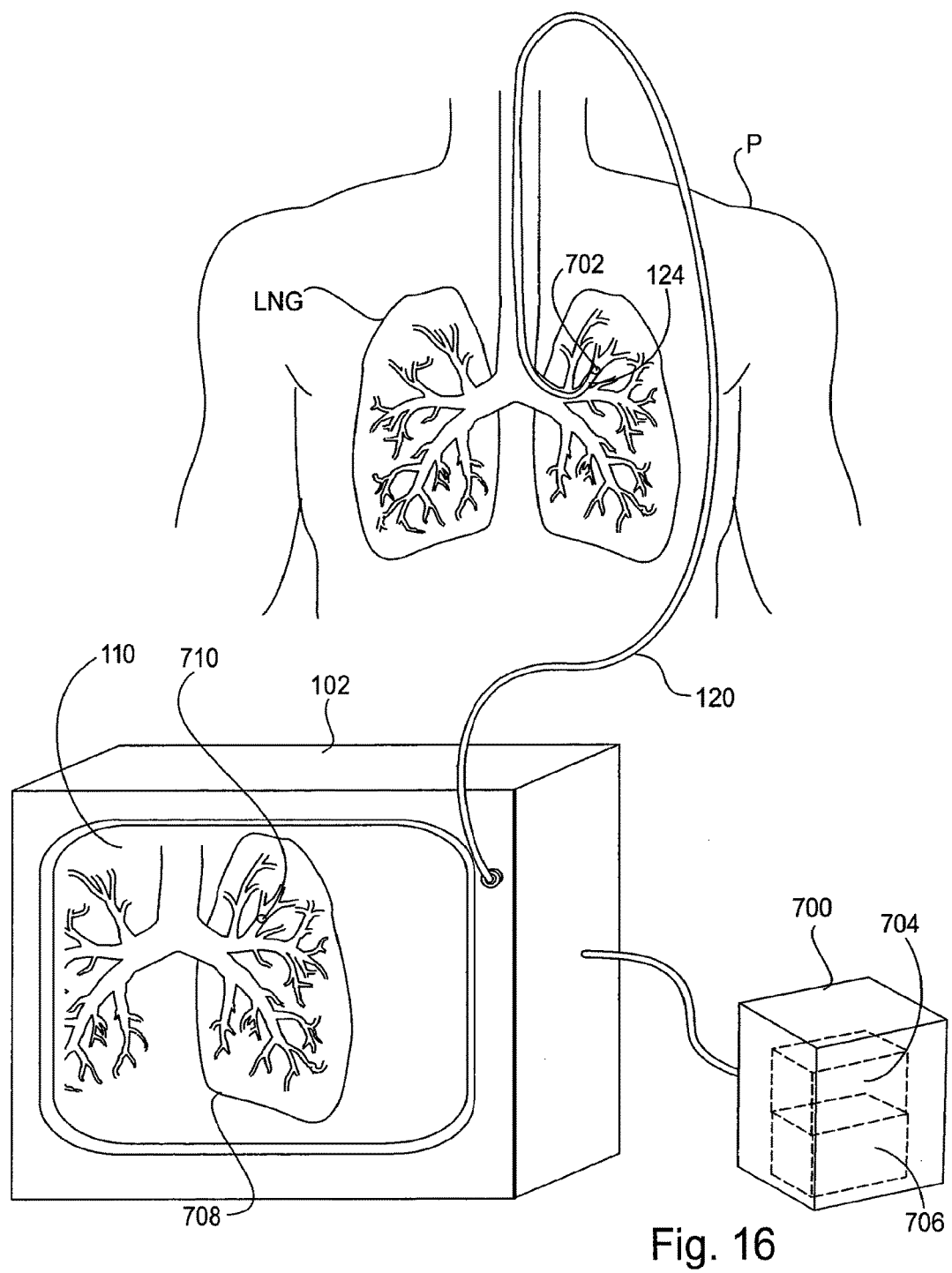
FIG. 16 is a schematic illustration of an EPD device and a measuring component comprising a mapping unit, wherein a pulmonary catheter is shown attached to the EPD device and advanced through the bronchial tree to a location in the patient's lungs.

In some embodiments, a measuring component 104 of the pulmonary diagnostic system 100 comprises an mapping unit 700, as shown in FIG. 16. Again, for clarity, the mapping unit 700 is illustrated as a separate attachable unit, however it may be appreciated that the unit 700 may be integral or internal to the EPD device 102. The mapping unit 700 is used for determining the position of the pulmonary catheter 120 as it is introduced and advanced through the bronchial passageways. Due to the multiple branchings of the bronchial anatomy, the position of the catheter 120 within the passageways may be difficult to determine and thus the lung compartment 154 to be measured may also be difficult to determine. With the use of the mapping unit 700, the position of the catheter 120 may be more readily visualized.

In one embodiment, a sensor 702 is used to track the position of the catheter 120 in the bronchial passageways. The sensor 702 is mounted on the catheter 120, typically near its distal end 124. The sensor 702 can be a simple magnetic type device or a frequency emitting device, to name a few. In another example, the sensor 702 could be an optical imaging element and coupled with artificial intelligence that tracks successive directional movements of the catheter tip, hence knowing its position at any given time. The mapping unit 700 may include mechanisms 704 for receiving the signal from the sensor and mechanisms 706 for processing the signal. Mechanisms for processing the signal include mechanisms for generating positioning data of the sensor 702 within the passageways and mechanisms for generating an image of the sensor positioned within the passageways reflecting the positioning data of the sensor 702. This is illustrated in FIG. 16. Here, the catheter 120 is attached to the EPD device 102 and its distal end 124 is introduced to a lung passageway of a patient P. A computer generated pulmonary anatomy image 708 is shown on the visual display 110. Further, a catheter positioning image 710 is shown within the anatomy image 708 reflecting the real-time position of the catheter 120 within the actual patient's anatomy. In this way, the target lung compartment may be more easily located and identified for later access if desired.

Data Receiving Components

Certain aspects of the data receiving components 115 have been presented above. The data receiving component 115 receives processed data from the EPD device 102 or any of the components 104 for output to the user. When the component 115 is the visual display 110, the processed data is presented in visual form. Alternatively, the component 115 may be a computer readable medium, such as disks, diskettes, CD-ROMs, tapes or the like. The computer readable medium may then be transported to another device, such as a computer, workstation or even another EPD device 102 for use. In any case, at some point the processed data is typically displayed in visual form. It may be appreciated that the possibilities of displaying measurement information in visual form are limitless. A few embodiments are presented as examples.

As previously described, the pulmonary diagnostic system is used to measure compartments of a lung, wherein a compartment could be an entire lobe, a segment or a subsegment and beyond. Although information generated from a compartment may be used in determining the level of disease of the compartment itself, comparison of the generated information to other information is also useful in diagnosis and assessment of disease. For example, information generated from a compartment may be compared with baseline information from the patient or to information from a healthy patient. For ease in comparison, both or multiple sets of information may be displayed in the visual display 110 simultaneously. Such display may be graphical, numerical or any other type. Further, information generated from one compartment may be compared with information from another similar compartment within the same patient. This concept may be extended to numerous compartments. Again, for ease in comparison, multiple sets of information may be displayed in the visual display 110 simultaneously. This in turn may allow the physician to rank the compartments in order of level of disease or in order of need for treatment. Similarly, information generated from one compartment may be compared with information from other types or sizes of compartments to determine the affect of each compartment on the others. Again, multiple sets of information may be displayed in the visual display 110 simultaneously for this purpose.

In addition, as described in relation to the imaging unit 600 and mapping unit 700, visual images of the lung anatomy can be displayed on the visual display 110 as noted above. This may be useful in both diagnosis of disease, positioning of the pulmonary catheter 120 and determining the affect of treatment.

Blockage Catheter

Figure 17A:
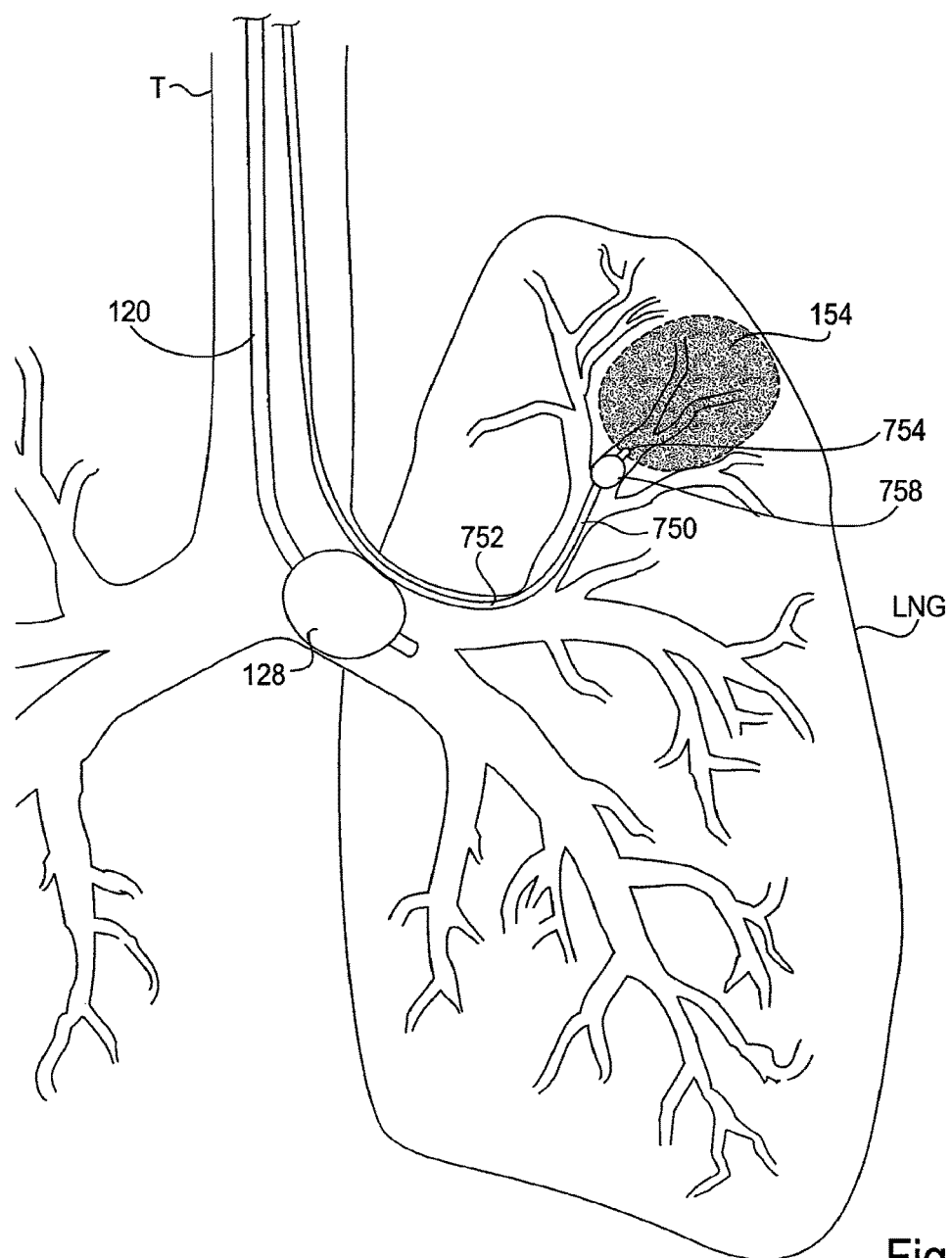
FIGS. 17A-17D depict embodiments of a blockage catheter.
Figure 17B:
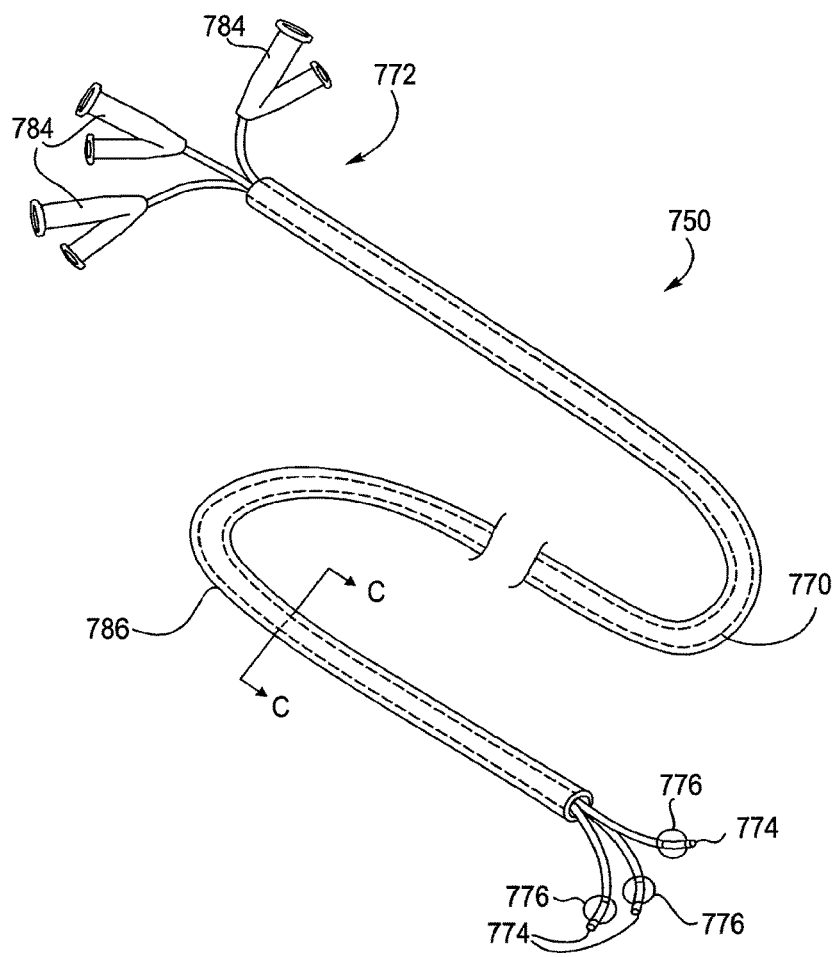
Figure 17C:
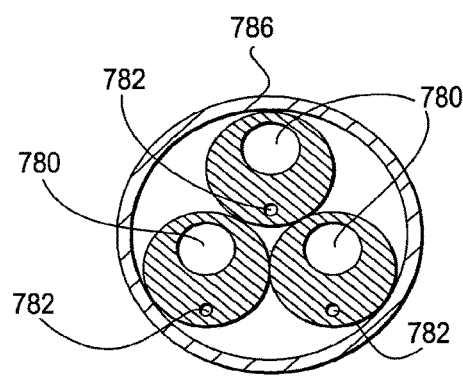
Figure 17D:
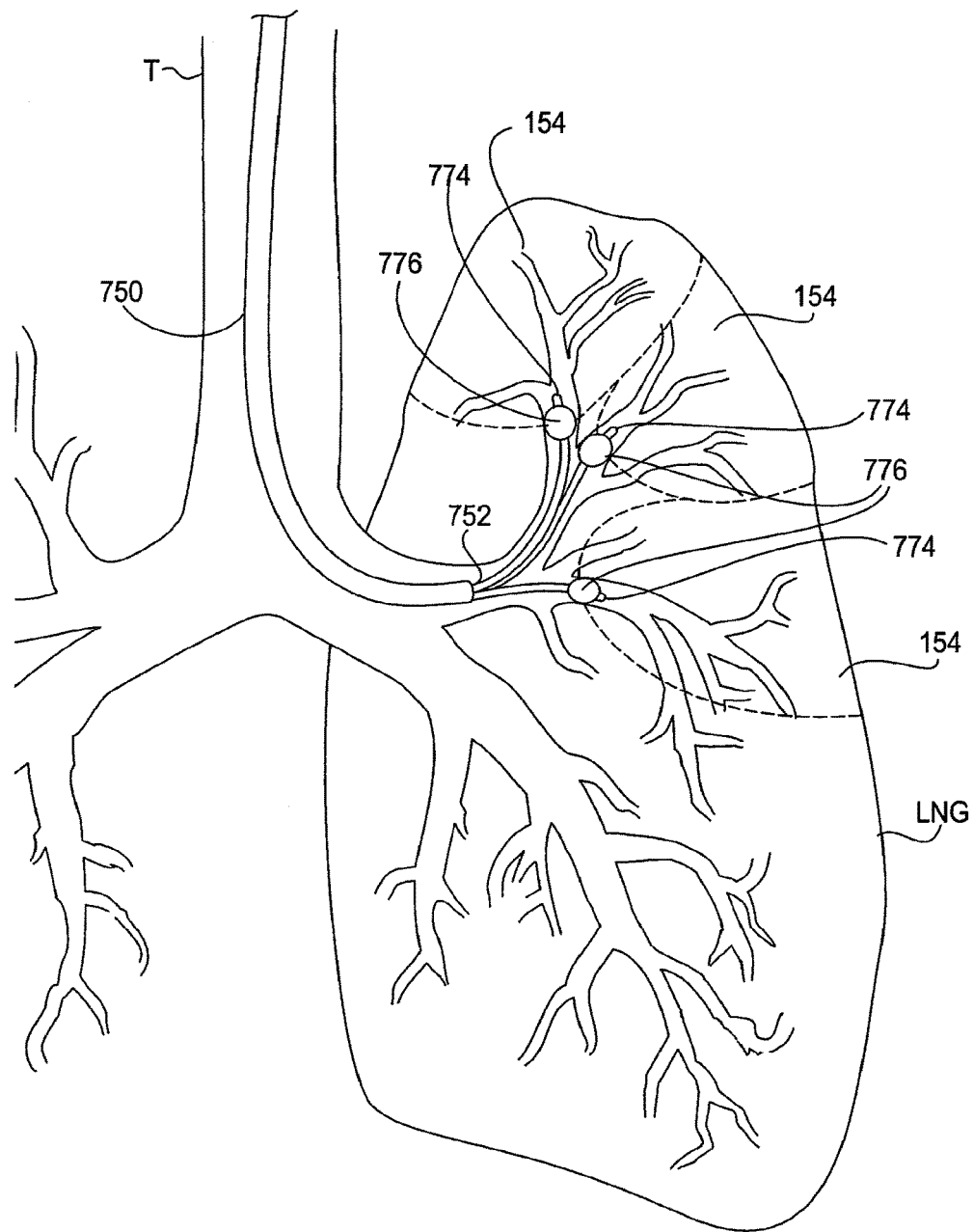

Once sufficient diagnostic testing, imaging and evaluation has been performed on the lung compartments 154, a treatment protocol may be determined. In some cases, lung volume reduction may be prescribed. To test the effects of such reduction prior to actual treatment, the lung passageway which leads to the lung compartment to be reduced may be temporarily occluded with a blockage catheter. Optionally this temporary occlusion with a blockage catheter may itself be the diagnostic test. One embodiment, shown in FIG. 17A, illustrates the blockage catheter 750 as comprising a catheter body 752 having a proximal end 756, a distal end 754, and an inflatable occlusion balloon 758 near its distal end 754. The blockage catheter 750 may have a smaller outer diameter than the access catheter 10 or other pulmonary catheters 120 which have lumens of significant diameter for various testing purposes. Here, lumens may simply be sized for inflation of the occlusion balloon 758 or passage of a guidewire. Another embodiment, shown in FIGS. 17B-D, illustrates the blockage catheter 750 as comprising a catheter body 770 having a proximal end 772 and a multiplicity of distal ends 774, each distal end 774 having an inflatable occlusion balloon 776 mounted thereon. Typically, a separate guidewire lumen 780 and balloon inflation lumen 782 within the catheter body 770 are present from the proximal end 772 to each distal end 774. End connectors 784 may be present near the proximal end 772 for access to each lumen 780, 782. In addition, an outer sleeve 786 encasing the catheter body 770 unites the distal ends 774 for introduction purposes. FIG. 17C shows a cross-section of the distal ends 774 of the catheter body 770. It may be appreciated that the catheter body 770 may comprise separate catheters, each having a guidewire lumen 780, inflation lumen 782 and occlusion balloon 776, which are held together by the outer sleeve 786 or other means. Referring to FIG. 17D, placement of the blockage catheter 750 involves positioning each distal end 774 into a different lung passageway. Each distal end 774 may be independently positioned with the use of a guidewire. Thus, a number of lung compartments 154 may be simultaneously isolated by the blockage catheter 750.

When the blockage catheter 750 is in place and the lung passageway(s) occluded by the balloon(s), the affected lung compartment 154 will be isolated from the remainder of the lung. At this point, testing, imaging and evaluation of the overall lung performance may be undertaken to measure the effects of the isolation. Such techniques would include, for example, CT scanning, spirometry, or plethysmography to obtain images, spirometry data or plethysmography data, respectively. This in turn reflects the effect of reduction of that isolated compartment. Similarly, such testing and evaluation may be performed on specific segments of the lung for assessing particular regions of the lung. Referring back to FIG. 17A, such testing with a pulmonary catheter 120 while the blockage catheter 750 is in place is illustrated. The blockage catheter 750 may be introduced through a lumen in the pulmonary catheter 120 or the blockage catheter 750 may simply lie in parallel with the pulmonary catheter 120. If the pulmonary catheter 120 utilizes an occlusion member 128, the member 128 may seal against the lumen and the catheter body 752 of the blockage catheter 750. Both the blockage catheter 750 and pulmonary catheter 120, or any additional catheters, may be simultaneously connected to the EPD device 100 if desired. The results of such assessment may determine the most effective course of treatment.

Treatment Unit

Figure 18:
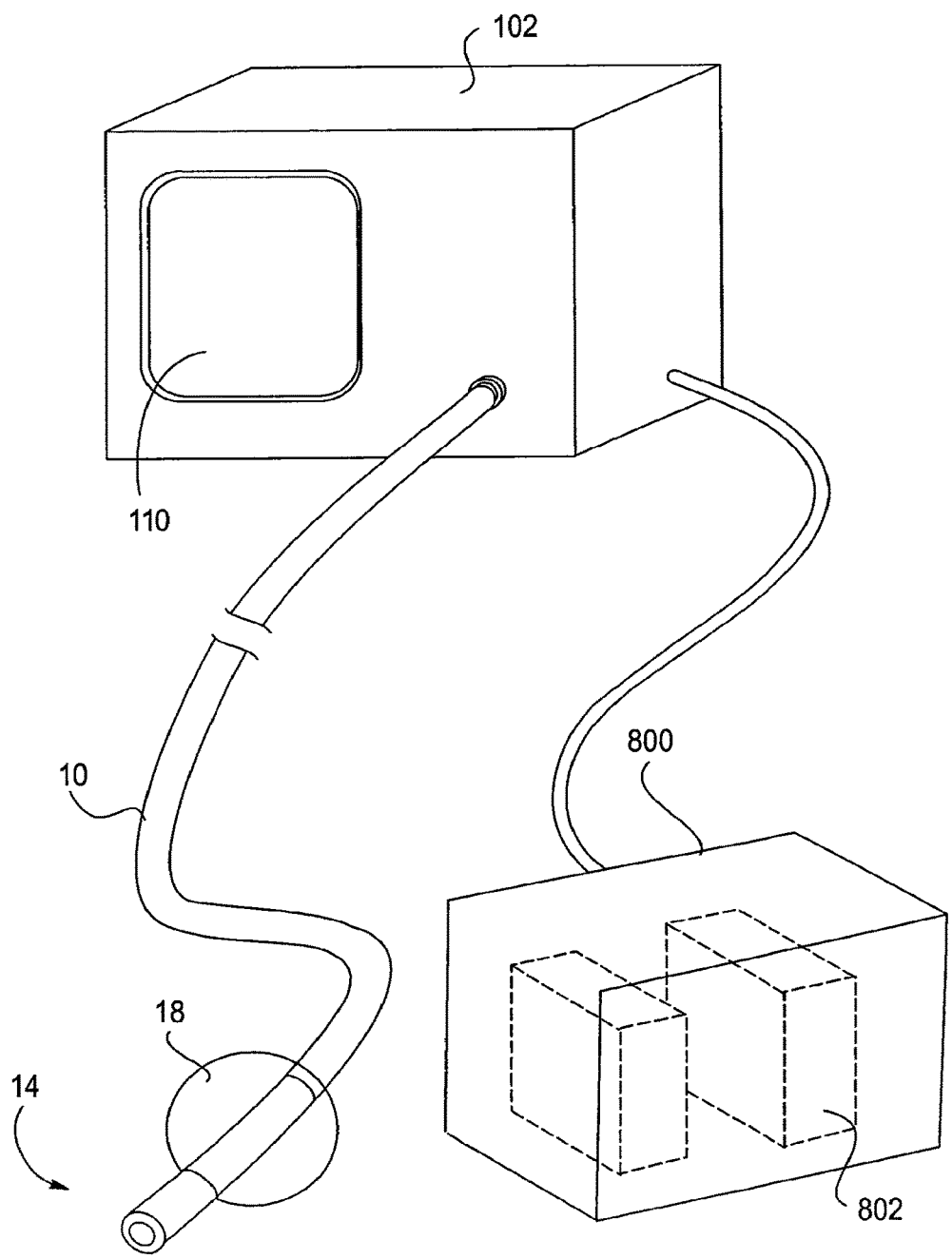
FIG. 18 is a schematic illustration of an EPD device and a measuring component comprising a treatment unit, wherein a treatment catheter is shown attached to the EPD device.

In some embodiments, a measuring component 104 of the pulmonary diagnostic system 100 may comprise a treatment unit 800, as shown in FIG. 18. Again, for clarity, the treatment unit 800 is illustrated as a separate attachable unit, however it may be appreciated that the unit 800 may be integral or internal to the EPD device 102. The treatment unit 800 may be used to perform a lung volume reduction procedure on a lung compartment 154. In this case, the unit 800 would include mechanisms 802 for performing lung volume reduction. This typically involves aspirating the contents of the compartment after isolating the compartment from the remainder of the anatomy. This is typically achieved by introducing the distal end 14 of the access catheter 10 endotracheally to the target compartment 154. Once in position, the compartment may be isolated by occluding the air passageway, such as by inflating the occlusion balloon 18 within the passageway. The target compartment may then be collapsed by aspirating air, and any other gases or liquids that may have been introduced, from the compartment, such as through a lumen in the access catheter 10. Optionally, the passageway may then be sealed, for example by deploying a plug within the air passageway. Some sealing methods include the use of tissue adhesives, occlusive balloons, expanding occlusive structures, the use of energy-induced tissue fusion and the like. Preferred embodiments of various types of treatments are described in copending U.S. patent application Ser. Nos. 09/425,272, 09/347,032, 09/606,320, 09/523,016, 09/699,302, all of which are incorporated as a reference herein for all purposes. After treatment, the affect of treatment may be evaluated by some of the measurement methods described above.

Figure 19:
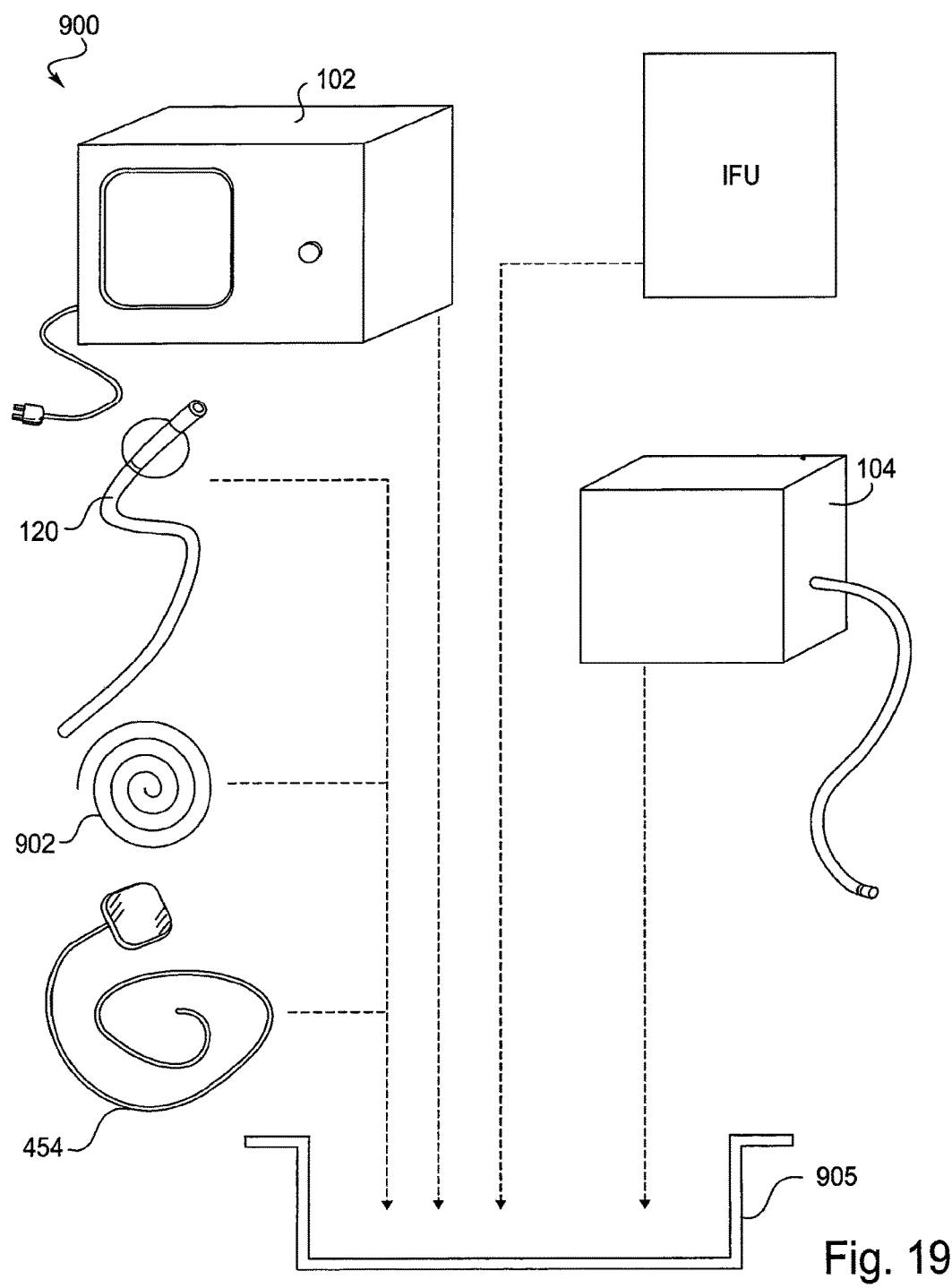
FIG. 19 illustrates a kit constructed in accordance with the principles of the present invention.

Kits 900 according to the present invention comprise any number of items related to the pulmonary diagnostic system described and instructions for use IFU. As shown in FIG. 19, such kits 900 typically include the EPD device 102 and instructions for use IFU setting forth methods according to the present invention. The EPD device 102 may have one or more measuring components disposed internally, however the kit 900 may also include one or more measuring components 104 as shown. Optionally, the kits 900 may further include any of the other system components described above, such as one or more pulmonary catheters 120, guidewires 902, or a variety of accessories, such as a receiver 454. Some or all kit components will usually be packaged together in a pouch 905 or other conventional medical device packaging. Usually, those kit components, such as a pulmonary catheter 120, which will be used in performing the procedure on the patient will be sterilized and maintained within the kit. Optionally, separate pouches, bags, trays or other packaging may be provided within a larger package, where the smaller packs may be opened separately to separately maintain the components in a sterile fashion.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A pulmonary diagnostic system comprising:
   a multi-lumen pulmonary catheter having a proximal end and a distal end, wherein the distal end comprises an inflatable occlusion balloon configured to isolate a lungcompartment from a remainder of the lung;
   a pulmonary diagnostic device comprising a transferring component configured to transfer fluids or gases to or from the lung,
   wherein the pulmonary diagnostic device is configured to receive measurement data from at least one sensor, and to coordinate the functioning of the pulmonary diagnostic device;
   a data receiving component;
   and one or more sensors disposed in or on the pulmonary catheter, said sensors generating measurement data reflecting respiratory features of the isolated lung compartment, wherein the respiratory features of the isolated lung compartment comprise pressure and flow;
   wherein the pulmonary diagnostic device further comprises an analyzing component configured to analyze the measurement data to generate processed measurement data, enable values of disease parameters reflective of an individual isolated lung compartment to be determined, and to calculate a resistance value of the isolated lung compartment based on the measurement data reflecting pressure and flow;
   wherein the pulmonary diagnostic device further is configured to coordinate the transfer of the fluids or gases between the components of the pulmonary diagnostic device and the lung, the passage of data between the sensor and the pulmonary diagnostic device, and the passage of data between the pulmonary diagnostic device and the data receiving component;
   wherein the system is configured to determine pressure and flow of the isolated lung compartment during unassisted breathing; and
   wherein the data receiving component is configured to receive the processed measurement data; and
   wherein the data receiving component comprises a visual display which is configured to simultaneously display resistance values corresponding to multiple lung compartments in visual form; and
   wherein the system is configured to rank the multiple lung compartments based on a level of disease or a need for treatment.

2. A system as in claim 1, wherein the respiratory features comprise velocity, oxygen concentration, or noble gas concentration.

3. A system as in claim 1, wherein the pulmonary diagnostic device converts the measurement data into a computer readable format.

4. A system as in claim 1, wherein the transferring component comprises a source of the fluid or gas and a means for generating flow of the fluid or gas.

5. A system as in claim 4, wherein the gas comprises air, oxygen, carbon dioxide, noble gas, radiopaque gas, polarized gas or a mixture of any of these.

6. A system as in claim 1, wherein the catheter is sized and has sufficient torque response and pushability to permit endotracheal introduction and intraluminal advancement through a bronchus of the lung.

7. A system as in claim 1, wherein pulmonary catheter has a proximal end connectable with the device and a distal tip and wherein the sensor is disposed near the distal tip.

8. A system as in claim 1, wherein the sensor is disposed within the device.

9. The system of claim 1, wherein at least one lumen of the multi-lumen catheter is in fluid communication with the inflatable occlusion balloon.

10. The pulmonary diagnostic system of claim 1 further comprising: an introducing element selected from the group consisting of a primary tracheal tube, a bronchoscope, a visualizing endotracheal tube and a guidewire, said introducing element being configured to introduce the catheter to a lung.

11. The pulmonary diagnostic system of claim 1, wherein the analyzing component is configured to calculate the resistance value of the isolated lung compartment based on pressure divided by volumetric flow rate.

12. The pulmonary diagnostic system of claim 11, wherein the analyzing component is configured to calculate volume data based on the measurement data reflecting flow.

13. The pulmonary diagnostic system of claim 1 further comprising a second inflatable occlusion balloon; wherein the system is configured to simultaneously isolate the multiple lung compartments.

14. The pulmonary diagnostic system of claim 1, wherein the analyzing component is configured to calculate a compliance value of the isolated lung compartment.

* * * * *